United States Patent [19]
Shi et al.

[11] Patent Number: 5,755,999
[45] Date of Patent: May 26, 1998

[54] BLUE LUMINESCENT MATERIALS FOR ORGANIC ELECTROLUMINESCENT DEVICES

[75] Inventors: Jianmin Shi, Webster; Chin H. Chen, Mendon; Kevin P. Klubek, Rochester, all of N.Y.

[73] Assignee: Eastman Kodak Company, Rochester, N.Y.

[21] Appl. No.: 857,747

[22] Filed: May 16, 1997

[51] Int. Cl.$^6$ .............................. C09K 11/06; C07F 5/06
[52] U.S. Cl. .................. 252/301.16; 252/301.17; 252/301.25; 252/301.36
[58] Field of Search .............. 252/301.16, 301.17, 252/301.25, 301.32, 301.36; 428/917

[56] References Cited

U.S. PATENT DOCUMENTS

| | | | |
|---|---|---|---|
| 5,141,671 | 8/1992 | Bryan et al. | 252/301.16 |
| 5,151,629 | 9/1992 | VanSlyke | 313/504 |
| 5,256,945 | 10/1993 | Imai et al. | 313/504 |

*Primary Examiner*—Johann Richter
*Assistant Examiner*—Ebenezer Sackey
*Attorney, Agent, or Firm*—Raymond L. Owens

[57] ABSTRACT

A luminescent material including a compound of the formula:

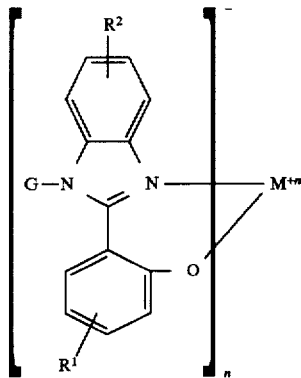

where:

n is an integer of 2 or 3;

M is a divalent metal or a trivalent metal;

G is a substituted or unsubstituted aryl group or a substituted or unsubstituted heteroaryl group, both the aryl and the heteroaryl groups having 6 to 24 carbon atoms, wherein the substituted aryl or heteroaryl group is an alkyl, haloalkyl group having 1-8 carbon atoms, an alkoxy or haloalkoxy group having 1-18 carbon atoms, halogen, cyano, amino, amido, sulfonyl, carbonyl, aryl, or heteroaryl; and $R^1$ and $R^2$ are individually hydrogen, an alkyl or haloalkyl group having 1-18 carbon atoms, halogen, cyano, amono, amido, sulfonyl, carbonyl, and 5-24 atoms necessary to complete a fused aromatic ring.

8 Claims, 2 Drawing Sheets

BLUE LUMINESCENT MATERIALS FOR ORGANIC ELECTROLUMINESCENT DEVICES

CROSS REFERENCE TO RELATED APPLICATION

Reference is made to commonly-assigned U.S. patent application Ser. No. 08/857,746 filed concurrently herewith, entitled "Efficient Blue Organic Electroluminescent Devices" by Shi et al, the teaching of which is incorporated herein.

FIELD OF THE INVENTION

This invention relates to novel luminescent materials, and more particularly, this invention relates to a novel class of luminescent materials of metal chelates.

Organometallic complexes luminescent materials for use in organic electroluminescent (EL) devices have been reported. Commonly-assigned U.S. Pat. No. 4,720,432 issued Jan. 19, 1988, discloses the efficient organic EL devices using the organometallic complex, metal chelates of 8-quinolinolato ligands, as a luminescent medium. In commonly-assigned U.S. Pat. No. 5,141,671, issued Aug. 25, 1992, discloses a blue emitting luminescent materials belong to the metal chelates of substituted 8-quinolinolato ligands. European patent application EP 0,652,273 (A1), published on May 10, 1995, disclosed an organic luminescent material for electroluminescent devices which use an organometallic complex of 2-(o-hydroxyphenyl)-benzoxazole or benzothiazole. European patent application EP 0.700,917 (A2), published on Mar. 13, 1996, disclosed a new class of organic luminescent material for use in electroluminescent devices in which the organometallics are prepared by mixing 2-(o-hydroxyphenyl)benzoxazole or benzothiazole complexes and other ligands with metals.

Further improvement in organic EL devices such as color, stability, efficiency and fabrication methods have been disclosed in U.S. Pat. Nos.: 4,356,429; 4,539,507; 4,720,432; 4,885,211; 5,151,629; 5,150,006; 5,141,671; 5,073,446; 5,061,569; 5,059,862; 5,059,861; 5,047,687; 4,950,950; 4,769,292, 5,104,740; 5,227,252; 5,256,945; 5,069,975, and 5,122,711; 5,366,811; 5,126,214; 5,142,343; 5,389,444; 5,458,977; 5,554,450; 5,593,788.

SUMMARY OF THE INVENTION

It is an object of the present invention to provide a novel class of luminescent metal chelates.

In the present invention, it has been found that a class of novel luminescent materials belonging to the organometallic complexes having o-(N-aryl-2-benzimidazolyl)phenol ligands is capable of producing highly efficient blue electroluminescence. These materials can also be used to produce EL devices with a wide range of visible colors.

The above object is achieved in a luminescent material including a compound of the formula I:

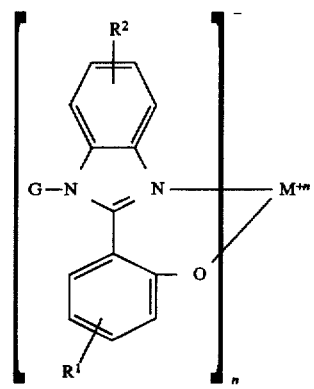

where:

n is an integer of 2 or 3;

M is a divalent metal or a trivalent metal;

G is a substituted or unsubstituted aryl group or a substituted or unsubstituted heteroaryl group, both the aryl and the heteroaryl groups having 6 to 24 carbon atoms, wherein the substituted aryl or heteroaryl group is an alkyl, haloalkyl group having 1–8 carbon atoms, an alkoxy or haloalkoxy group having 1–18 carbon atoms, halogen, cyano, amino, amido, sulfonyl, carbonyl, aryl, or heteroaryl; and $R^1$ and $R^2$ are individually hydrogen, an alkyl or haloalkyl group having 1–18 carbon atoms, halogen, cyano, amono, amido, sulfonyl, carbonyl, and 5–24 atoms necessary to complete a fused aromatic ring.

In accordance with the present invention, a novel class of chelates has been discovered having o-(N-aryl-2-benzimidazolyl)phenol ligands. The invention is particularly suitable for use in organic electroluminescent (EL) devices but is also suitable for use as a electron transporting carrier which can also be used in EL devices and other electro-optical devices. Moreover, it can be used in photoconductive elements particularly suitable in electrophotographic copying applications.

In one aspect, this invention relates to a novel class of luminescent materials of metal chelates having o-(N-aryl-2-benzimidazolyl)phenol ligands.

In another aspect, this invention relates to a novel class of luminescent materials of metal chelates having o-(N-aryl-2-benzimidazolyl)phenol ligands and capable of emitting visible light luminescence.

In a further aspect, this invention relates to a novel class of luminescent materials of metal chelates having o-(N-aryl-2-benzimidazolyl)phenol ligands and capable of using as components in organic EL devices.

BRIEF DESCRIPTION OF THE DRAWINGS

These and other advantages of this invention can be better appreciated by reference to the following detailed description considered in conjunction with the drawings in which.

DETAILED DESCRIPTION OF THE PREFERRED EMBODIMENTS

Figure 1:
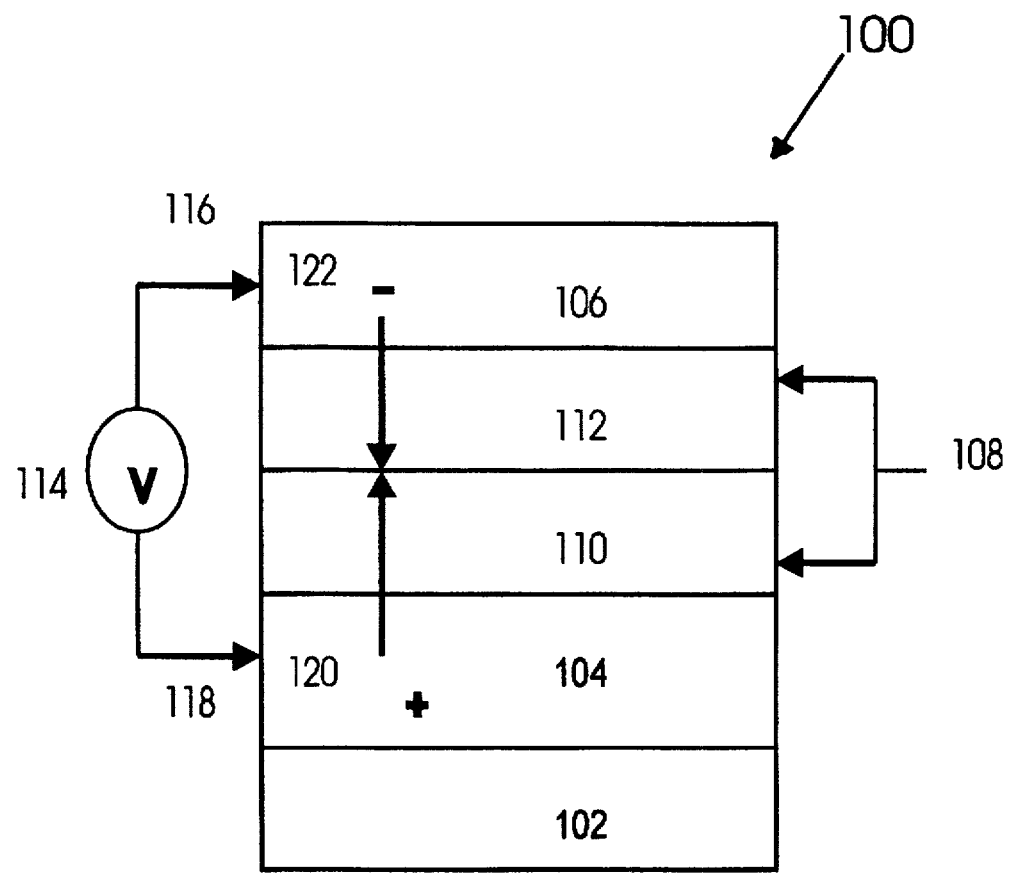
FIGS. 1, 2, and 3 are schematic diagrams of the multilayer structures of preferred EL devices in accordance with the present invention.

The present invention is particularly suitable for use in EL devices and so those applications will now be discussed. An EL device 100 according to the invention is schematically illustrated in FIG. 1. The support is layer 102 which is an electrically insulating and optically transparent material such as glass or plastic. Anode 104 is separated from cathode 106 by an organic EL medium 108, which, as shown, consists of two superimposed layers of organic thin films. Layer 110 located on the anode forms a hole-transport layer of the organic EL medium. It will be understood that the term "medium" includes one or more layers. Located above the hole-transport layer is layer 112, which forms an electron-transport layer of the organic EL medium. The anode and the cathode are connected to an external AC or DC power source 114 by conductors 116 and 118, respectively. The power source can be pulsed, periodic, or continuous.

In operation, the EL device can be viewed as a diode which is forward biased when the anode is at a higher potential than the cathode. Under these conditions, holes (positive charge carriers) are injected from the anode into the hole-transport layer, and electrons are injected into the electron-transport layer. The injected holes and electrons each migrate toward the oppositely charged electrode, as shown by the arrows 120 and 122, respectively. This results in hole-electron recombination and a release of energy in part as light, thus producing electroluminescence.

The region where the hole and electron recombine is known as the recombination zone. The two-layer device structure is designed specifically to confine the recombination at the vicinity near the interface between the hole-transport and the electron-transport layer where the probability for producing electroluminescence is the highest. This recombination confinement scheme has been disclosed by Tang and Van Slyke [Applied Physics Letters, Volume 51, Page 913, 1987] and is done by choosing carrier injecting electrodes of suitable work-functions and transport materials of a proper carrier mobility. Away from this interface between the organic layers and in particular at or near the injecting electrodes, the recombination of hole and electron would generally be much less radiative due to the effect of radiative quenching by a conducting surface.

Figure 2:
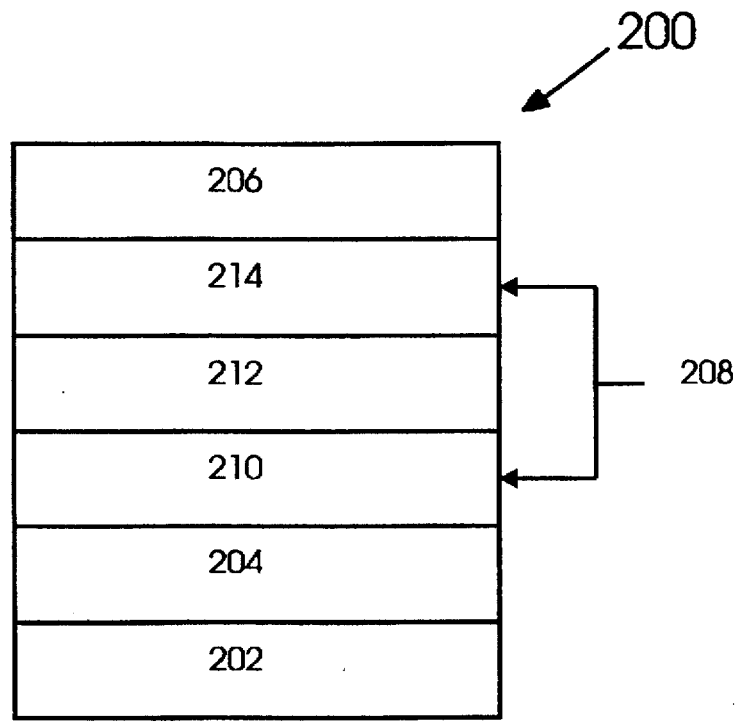

Organic EL device 200 shown in FIG. 2 is illustrative of another preferred embodiment of the invention. The insulating and transparent support is layer 202. The anode 204 is separated from the cathode 206 by an EL medium 208, which, as shown, consists of three superimposed layers of organic thin films. Layer 210 adjacent to anode 204 is the hole-transport layer. Layer 214 adjacent to cathode 206 is the electron-transport layer. Layer 212 which is in between the hole-transport layer and the electron transport layer is the luminescent layer. This luminescent layer also serves as the recombination layer where the hole and electron recombines.

The configurations of devices 100 and 200 are similar, except that an additional luminescent layer is introduced in device 200 to function primarily as the site for hole-electron recombination and thus electroluminescence. In this respect, the functions of the individual organic layers are distinct and can therefore be optimized independently. Thus, the luminescent or recombination layer can be chosen to have a desirable EL color as well as a high luminance efficiency. Likewise, the electron and hole transport layers can be optimized primarily for the carrier transport property.

Organic device 300 is illustrative of yet another preferred embodiment of the present invention. The insulating and transparent support is layer 302. The anode 304 is separated from the cathode 306 by an EL medium 308, which, as shown, consists of five superimposed layers of organic thin films. Located on top of the anode layer 304 are, in sequence, the hole-injection layer 310, the hole-transport layer 312, the luminescent layer 314, the electron-transport layer 316, and the electron-injection layer 318. The structure of device 300 is similar to device 200, except that a hole-injection layer and an electron injection layers are added to improve the injection efficiency of the respective anode and cathode. It is understood that an EL device may be constructed having either the hole or electron injection layer present in the organic EL medium without unduly compromising the device performance.

The substrate for the EL devices 100, 200, and 300 is electrically insulating and light transparent. The light transparent property is desirable for viewing the EL emission through the substrate. For applications where the EL emission is viewed through the top electrode, the transmissive characteristic of the support is immaterial, and therefore, any appropriate substrate such as opaque semiconductor or ceramic wafers can be used. Of course, it is necessary to provide in these device configurations a light transparent top electrode.

The composition of the organic EL medium is described as follows, with particular reference to device structure 300.

A layer containing a porphyrinic compound forms the hole injecting layer of the organic EL device. A porphyrinic compound is any compound, natural or synthetic, which is derived from or includes a porphyrin structure, including porphine itself. Any of the prophyrinic compounds disclosed by Adler, U.S. Pat. No. 3,935,031 or Tang U.S. Pat. No. 4,356,429, the disclosures of which are here incorporated by reference, can be employed.

Preferred porphyrinic compounds are those of structural formula (II):

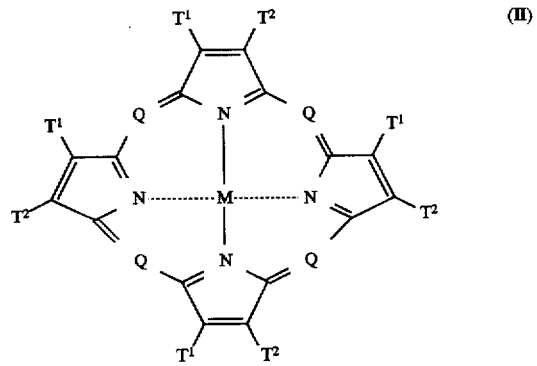

wherein

Q is —N= or —C(R)=;

M is a metal, metal oxide, or metal halide;

R is hydrogen, alkyl, aralkyl, aryl, or alkaryl; and $T^1$ and $T^2$ represent hydrogen or together complete a unsaturated six member ring, which can include substituents, such as alkyl or halogen. Preferred six membered rings are those formed of carbon, sulfur, and nitrogen ring atoms. Preferred alkyl moieties contain from about 1 to 6 carbon atoms while phenyl constitutes a preferred aryl moiety.

In an alternative preferred form the porphyrinic compounds differ from those of structural formula (II) by substitution of two hydrogens for the metal atom, as indicated by formula (III):

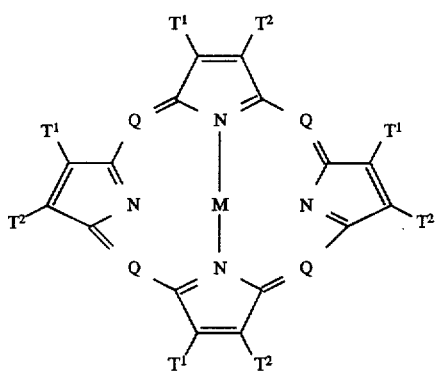

(III)

Highly preferred examples of useful porphyrinic compounds are metal free phthalocyanines and metal containing phthalocyanines. While the porphyrinic compounds in general and the phthalocyanines in particular can contain any metal, the metal preferably has a positive valence of two or higher. Exemplary preferred metals are cobalt, magnesium, zinc, palladium, nickel, and, particularly, copper, lead, and platinum.

Illustrative of useful porphyrinic compounds are the following:
Prophine
1,10,15,20-tetraphenyl-21H,23H-porphine copper (II)
1,10,15,20-tetrapheyl-21H,23H-porphine zinc (II)
Copper phthlocyanine
Chromium phthalocyanine fluoride The hole transporting layer of the organic EL device contains at least one hole transporting aromatic tertiary amine, where the latter is understood to be a compound containing at least one trivalent nitrogen atom that is bonded only to carbon atoms, at least one of which is a member of an aromatic ring. In one form the aromatic tertiary amine can be an arylamine, such as a monarylamine, diarylamine, triarylamine, or a polymeric arylamine. Exemplary monomeric triarylamines are illustrated by Klupfel et al U.S. Pat. No. 3,180,730. Other suitable triarylamines substituted with vinyl or vinyl radicals and/or containing at least one active hydrogen containing group are disclosed by Brantley et al U.S. Pat. Nos. 3,567,450 and 3,658,520.

Another class of aromatic tertiary amines are those which include at least two aromatic tertiary amine moieties. Such compounds include those represented by structural formula (IV).

(IV)

wherein
Q¹ and Q² are independently aromatic tertiary amine moieties and
G is a linking group such as an arylene, cycloalkylene, or alkylene group of a carbon to carbon bond.

A preferred class of triarylamines satisfying structural formula (IV) and containing two triarylamine moieties are those satisfying structural formula (V):

(V)

where
R¹ and R² each independently represents a hydrogen atom, an aryl group, or an alkyl group or R¹ and R² together represent the atoms completing a cycloalkyl group and R³ and R⁴ each independently represents an aryl group which is in turn substituted with a diaryl substituted amino group, as indicated by structural formula (VI):

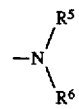

(VI)

wherein $R^5$ $R^6$ are independently selected aryl groups.

Another preferred class of aromatic tertiary amines are tetraaryldiamines. Preferred tetraaryldiamines include two diarylamino groups, such as indicated by formula (VII), linked through an arylene group:

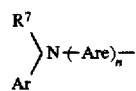

(VII)

wherein

Are is an arylene group, n is an integer of from 1 to 4, and

Ar, $R^7$, $R^8$, and $R^9$ are independently selected aryl groups.

The various alkyl, alkylene, aryl, and arylene moieties of the foregoing structural formulae (IV), (V), (VII), can each in turn be substituted. Typical substituents including alkyl groups, alkoxy groups, aryl groups, aryloxy groups, and halogen such as fluoride, chloride, and bromide. The various alkyl and alkylene moieties typically contain from about 1 to 6 carbon atoms. The cycloalkyl moieties can contain from 3 to about 10 carbon atoms, but typically contain five, six, or seven ring carbon atoms—e.g., cyclopentyl, cyclohexyl, and cycloheptyl ring structures. The aryl and arylene moieties are preferably phenyl and phenylene moieties.

Group I: Illustrative of useful hole transport compounds are the following:

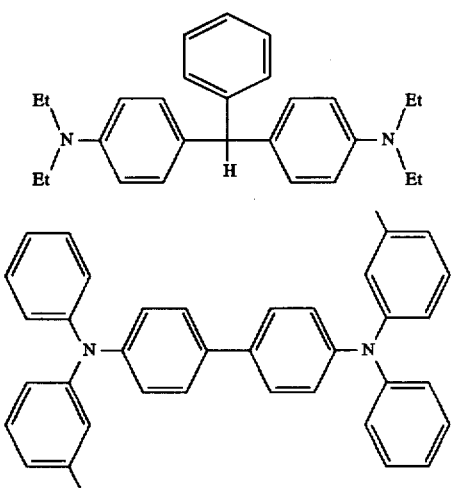

-continued

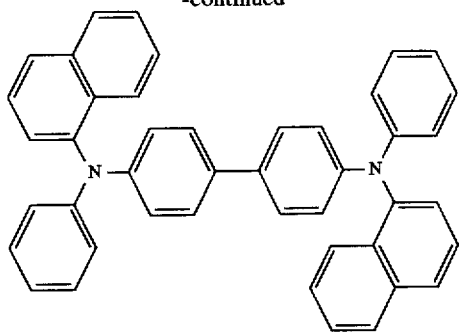

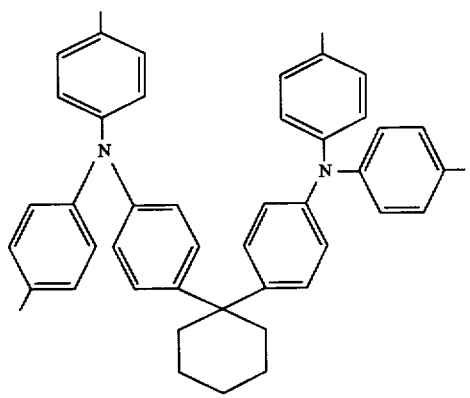

The luminescent layer of the organic EL medium comprises of a luminescent or fluorescent material where electroluminescence is produced as a result of electron-hole pair recombination in this region. In the simplest construction, the luminescent layer comprises of a single component, that is a pure material with a high fluorescent efficiency. A well known material is tris (8-quinolinato) Aluminum, (Alq), which produces excellent green electroluminescence. A preferred embodiment of the luminescent layer comprises a multi-component material consisting of a host material doped with one or more components of fluorescent dyes. Using this method, highly efficient EL devices can be constructed. Simultaneously, the color of the EL devices can be tuned by using fluorescent dyes of different emission wavelengths in a common host material. This dopant scheme has been described in considerable details for EL devices using Alq as the host material by Tang et [J. Applied Physics, Vol. 65, Pages 3610–3616, 1989; U.S. Pat. No. 4,769,292].

An important relationship for choosing a fluorescent dye as a dopant capable of modifying the hue of light emission when present in a host material is a comparison of their bandgap potential which is defined as the energy difference between the highest occupied molecular orbital and the lowest unoccupied molecular orbital of the molecule. For efficient energy transfer from the host to the dopant molecule, a necessary condition is that the bandgap of the dopant is smaller than that of the host material. An advantage of using a blue host such as benzazole is that its bandgap is sufficiently large to effect energy transfer to a range of commonly available fluorescent dyes emitting in the blue. These blue dopants includes coumarins, stilbenes, distyrylstilbenes, derivatives of anthracene, tetracene, perylene, and other conjugated benzenoids. Other dopants for EL emissions at longer wavelengths include coumarins, rhodamines and other green or red emitting fluorescent dyes.

Figure 3:
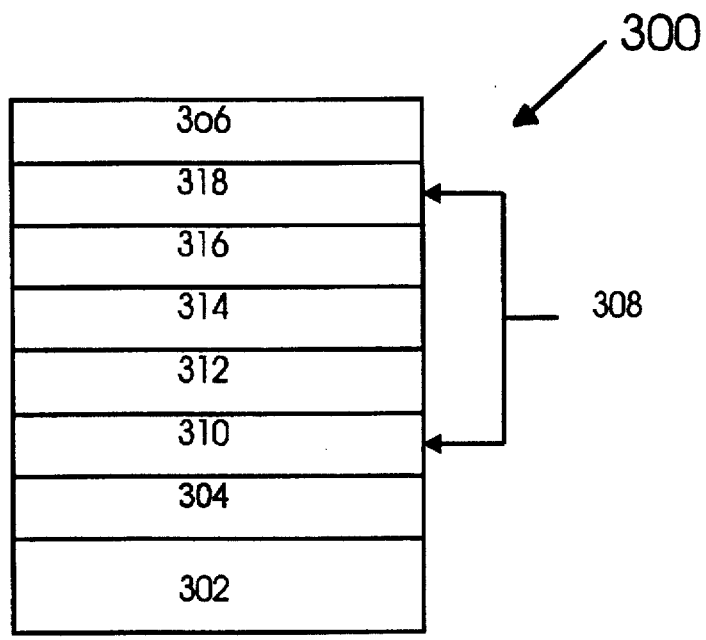

In the practice of the present invention, the host material forming the EL luminescent layer where light is emitted in response to electron-hole recombination comprises of a organometallic complex or a mixture of these organomatellic complexes represented by formula I. The dopants for the organometallic complexes may include fluorescent dyes as described above. Efficient blue electroluminescence can be readily obtained when this material is used in layer 112 of FIG. 1, layer 212 of FIG. 2 or layer 314 of FIG. 3.

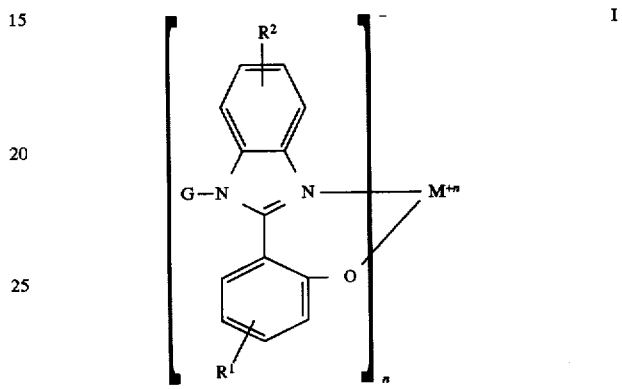

where:

n is an integer of 2 or 3;

M is a divalent metal or a trivalent metal;

G is a substituted or unsubstituted aryl group or a substituted or unsubstituted heteroaryl group, both the aryl and the heteroaryl groups having 6 to 24 carbon atoms, wherein the substituted aryl or heteroaryl group is an alkyl, haloalkyl group having 1–8 carbon atoms, an alkoxy or haloalkoxy group having 1–18 carbon atoms, halogen, cyano, amino, amido, sulfonyl, carbonyl, aryl, or heteroaryl;

$R^1$ and $R^2$ are individually hydrogen, an alkyl or haloalkyl group having 1–18 carbon atoms, halogen, cyano, amono, amido, sulfonyl, carbonyl, and 5–24 atoms necessary to complete a fused aromatic ring.

The following molecular structures constitute specific examples of preferred organic metallic complex satisfying the requirement of the invention:

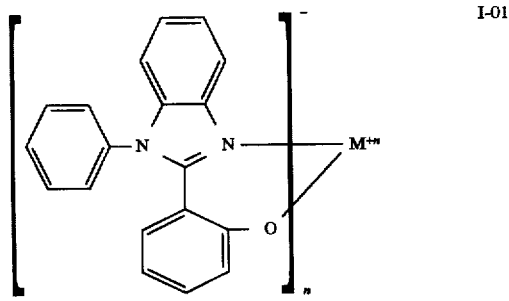

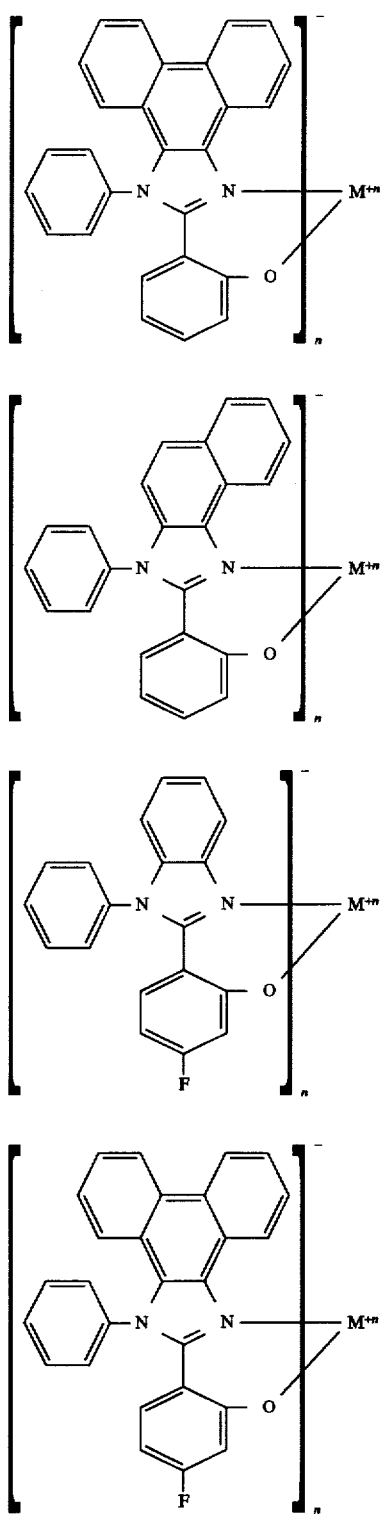
I-02
I-03
I-04
I-05
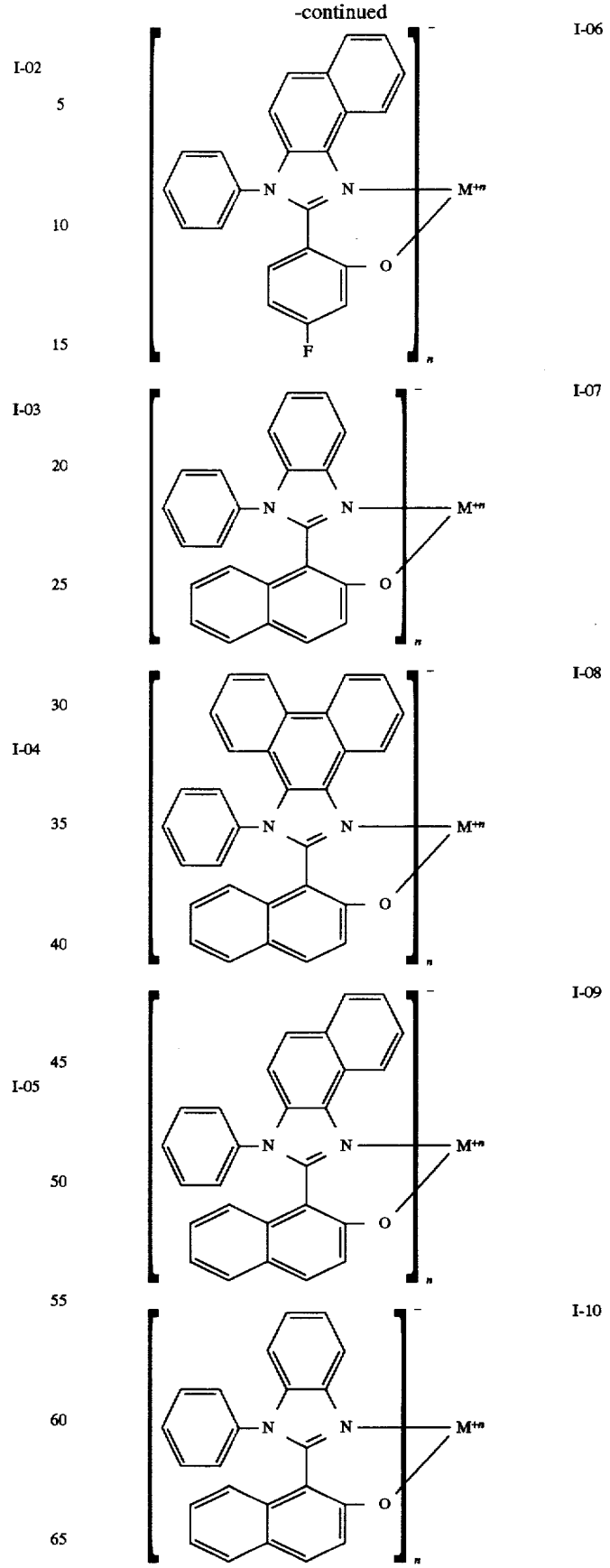
I-06
I-07
I-08
I-09
I-10

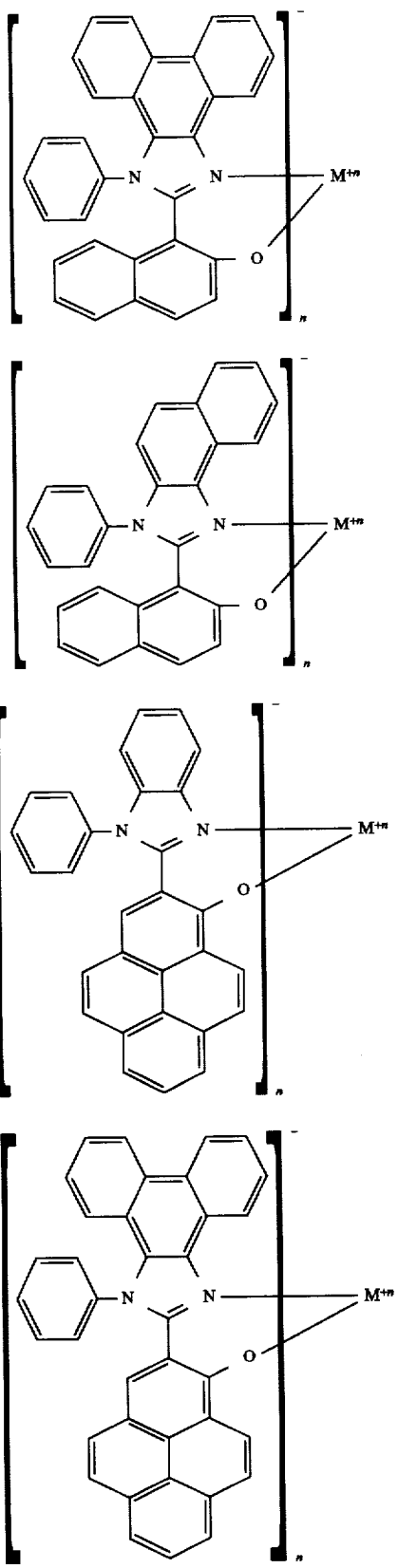
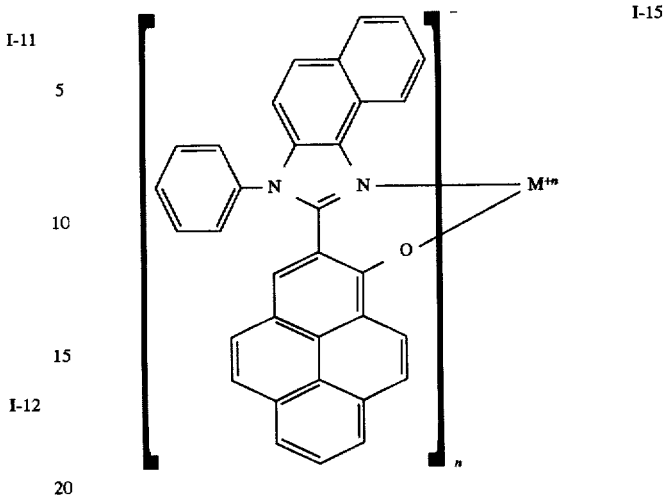
where:
n is an integer of 2 or 3;
M is a divalent metal or a trivalent metal;
When n=2, M is a divalent metal selected from the group consisting of Be, Mg, Sr, Ba, Ca, Zn, Cd, Hg, Pd, and Cu;
When n=3, M is a trivalent metal selected from the group consisting of Al, Ga, In, and Tl.
Group II:
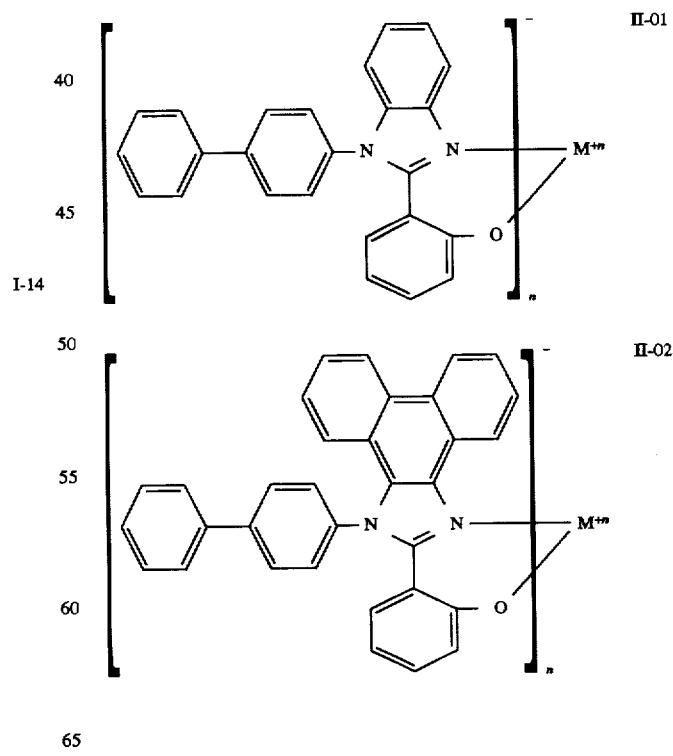

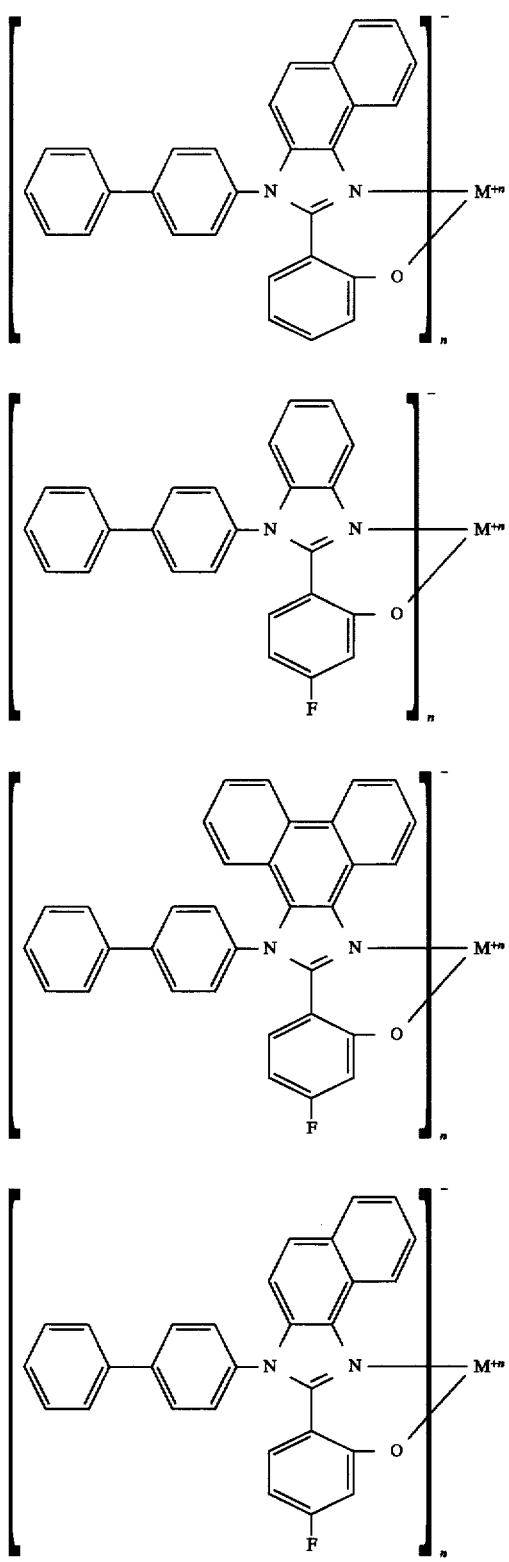
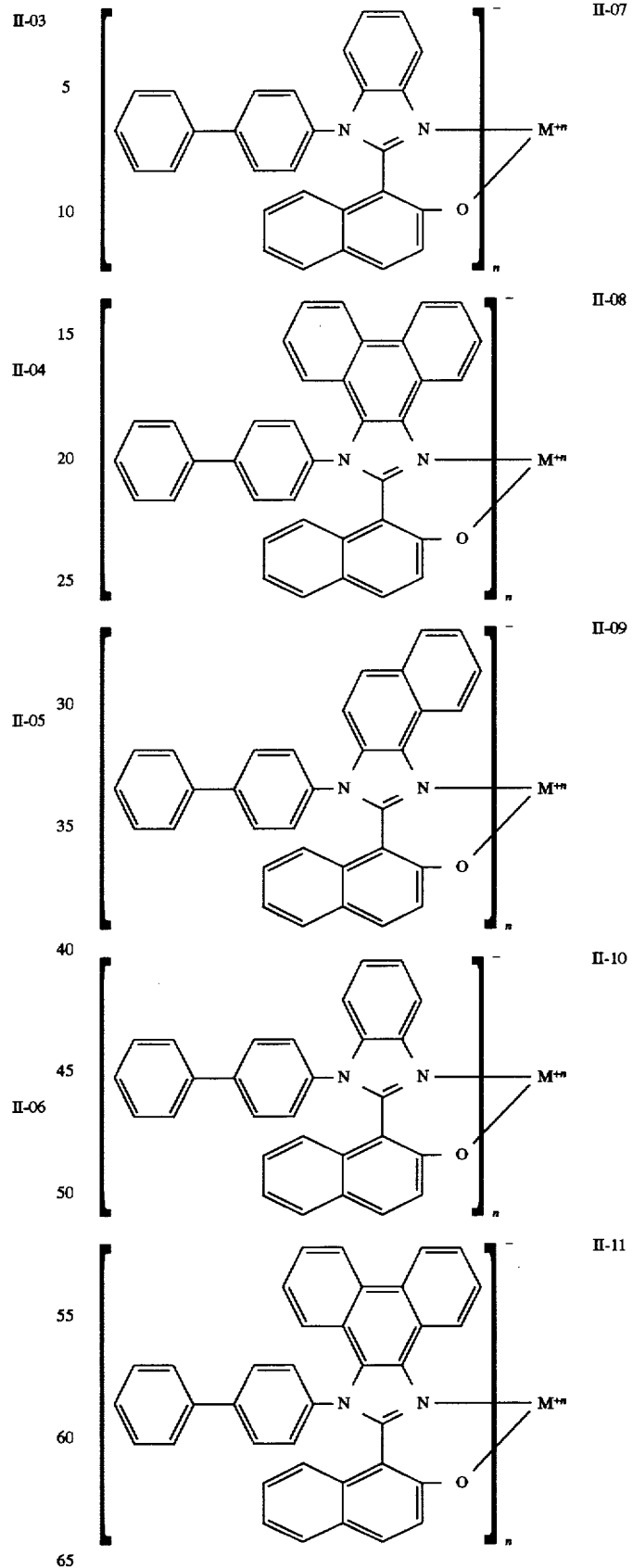

-continued
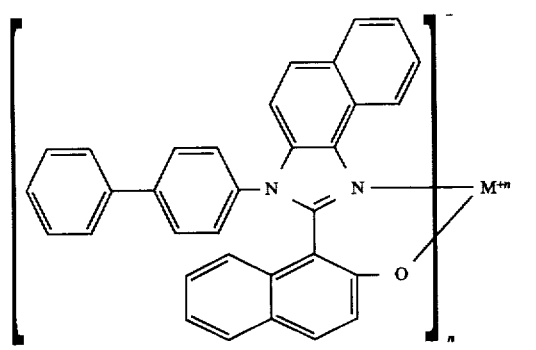
II-12
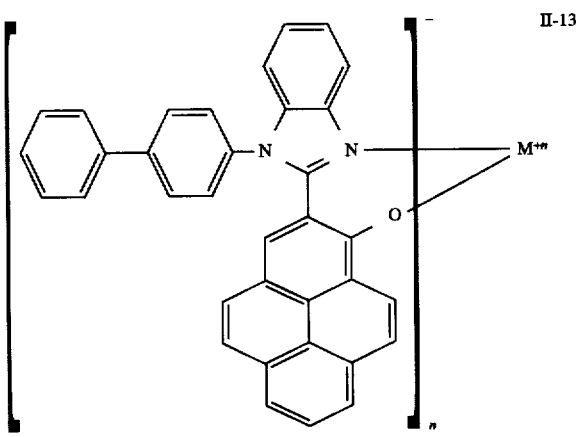
II-13
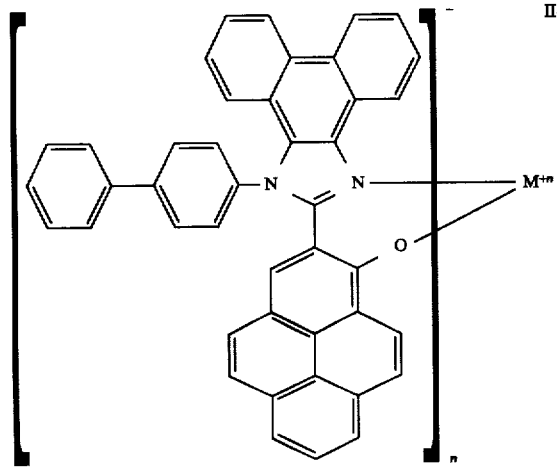
II-14
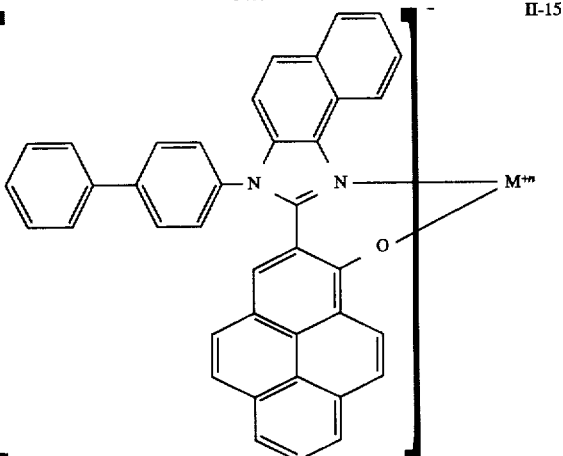
II-15
where:
  n is an integer of 2 or 3;
  M is a divalent metal or a trivalent metal;
  When n=2, M is a divalent metal selected from the group consisting of Be, Mg, Sr, Ba, Ca, Zn, Cd, Hg, Pd, and Cu;
  When n=3, M is a trivalent metal selected from the group consisting of Al, Ga, In, and Tl.
Group III:
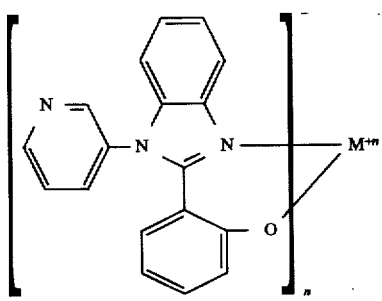
III-01
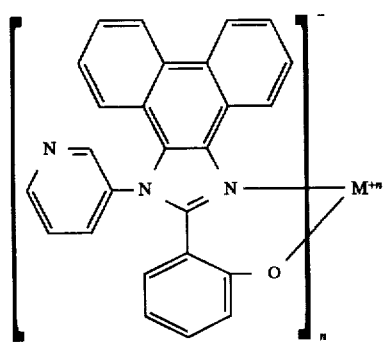
III-02

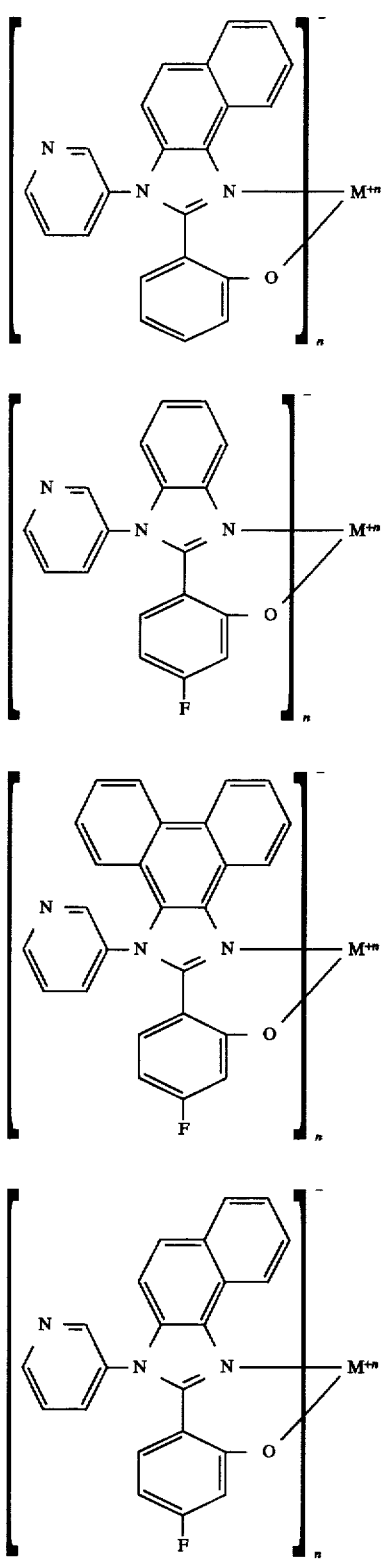
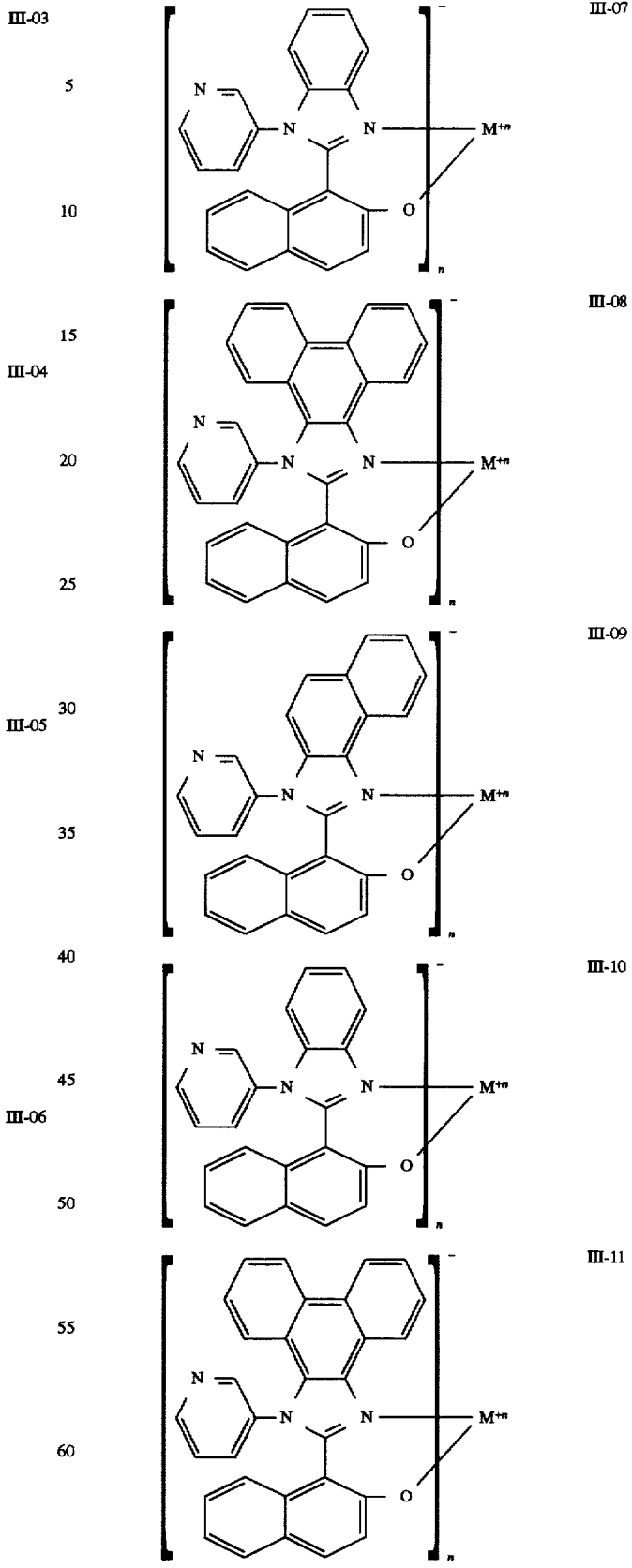

III-12
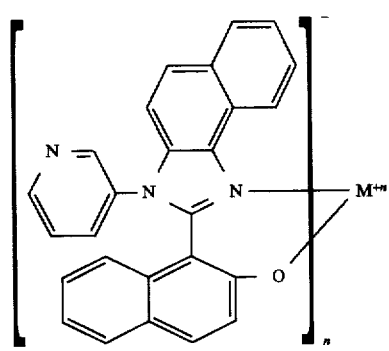
III-13
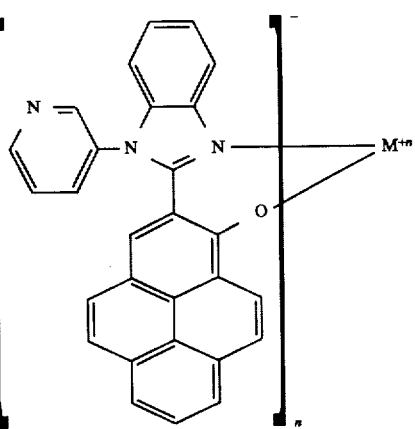
III-14
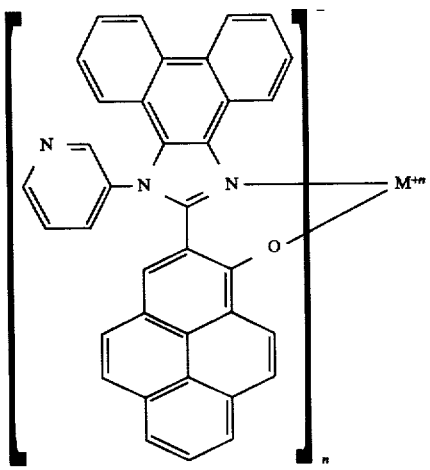
III-15
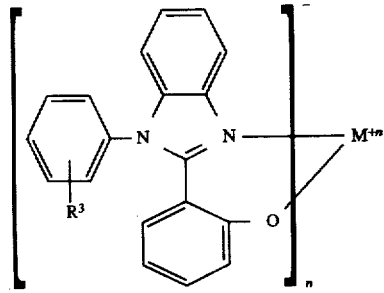
where:
n is an integer of 2 or 3;
M is a divalent metal or a trivalent metal;
When n=2, M is a divalent metal selected from the group consisting of Be, Mg, Sr, Ba, Ca, Zn, Cd, Hg, Pd, and Cu;
When n=3, M is a trivalent metal selected from the group consisting of Al, Ga, In, and Tl.
Group IV:
IV-01
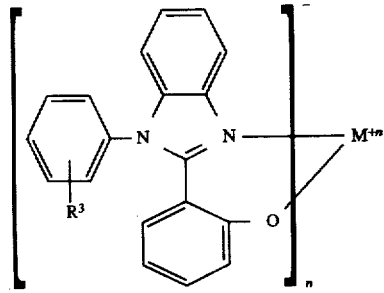
IV-02
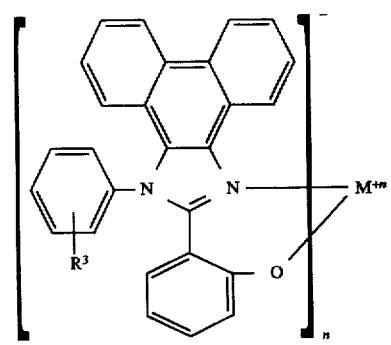

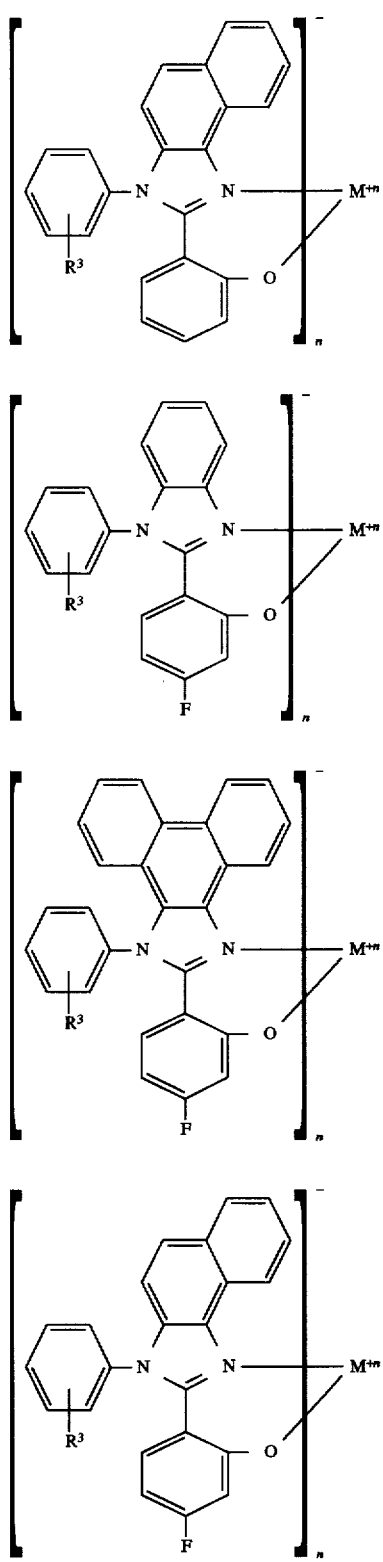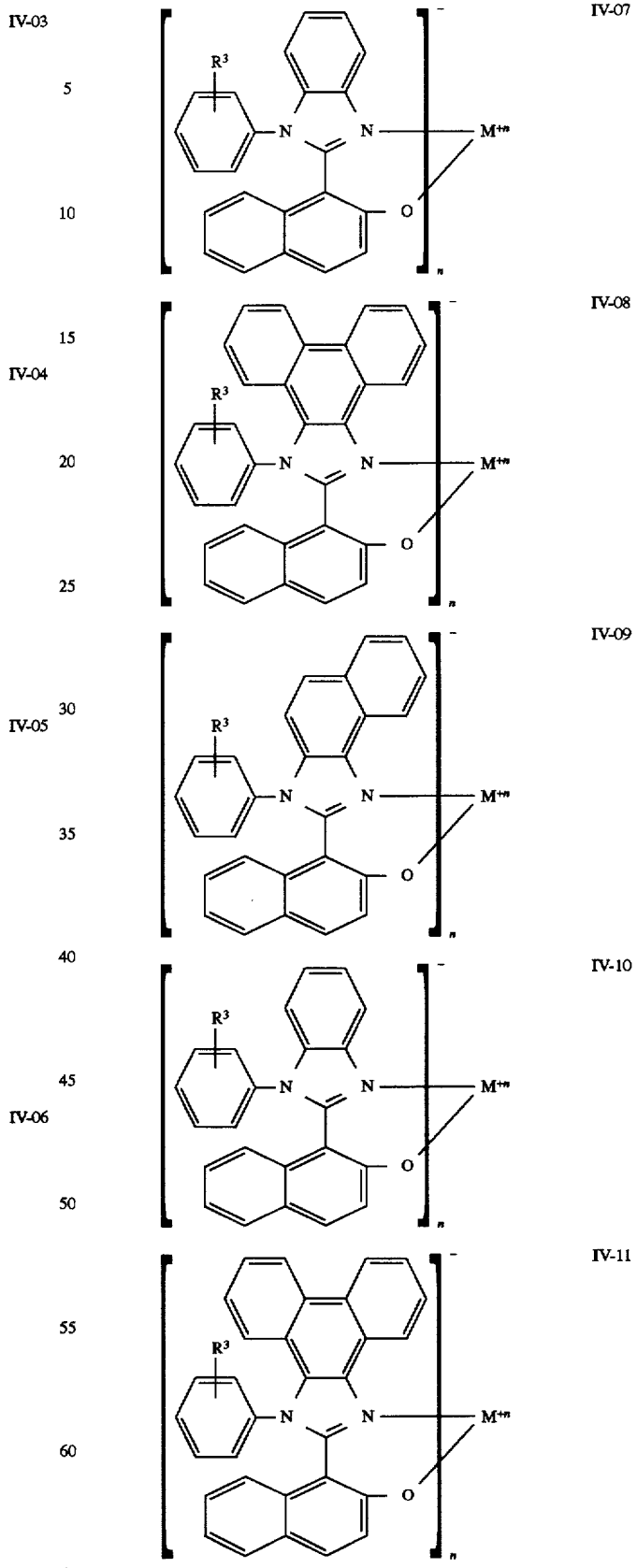

-continued

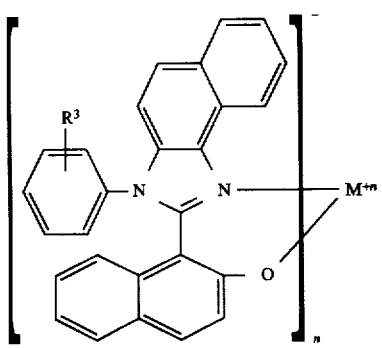
IV-12

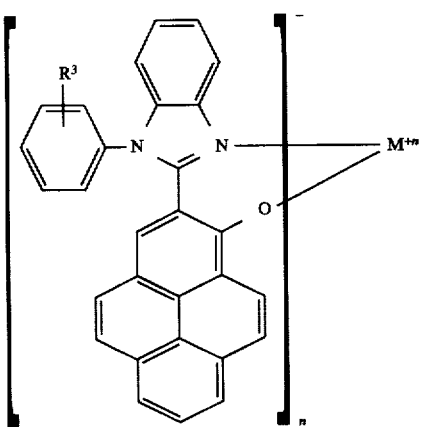
IV-13

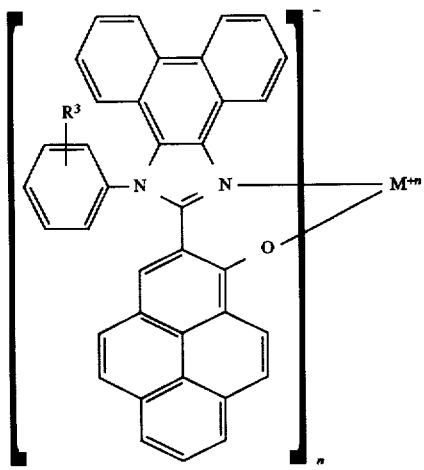
IV-14

-continued

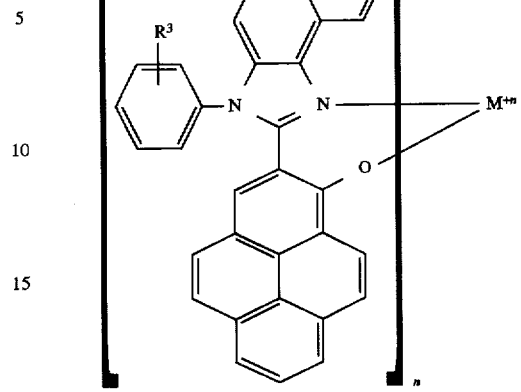
IV-15 where:

n is an integer of 2 or 3;

M is a divalent metal or a trivalent metal;

When n=2, M is a divalent metal selected from the group consisting of Be, Mg, Sr, Ba, Ca, Zn, Cd, Hg, Pd, and Cu;

When n=3, M is a trivalent metal selected from the group consisting of Al, Ga, In, and Tl;

$R^3$ is individually a halogen, an alkyl having 1–18 carbon atoms, cyano, sulfonyl, carbonyl, and 5–24 atoms necessary to complete a fused aromatic ring.

Group V:

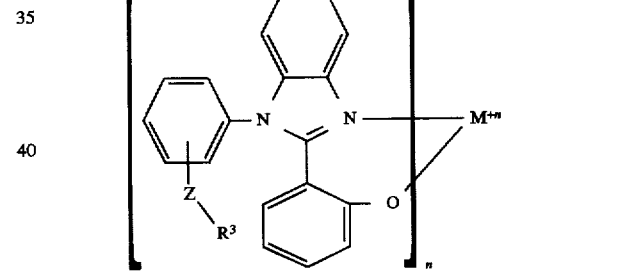
V-01

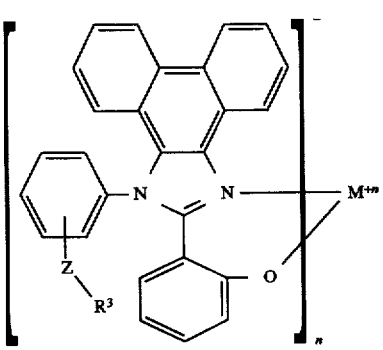
V-02

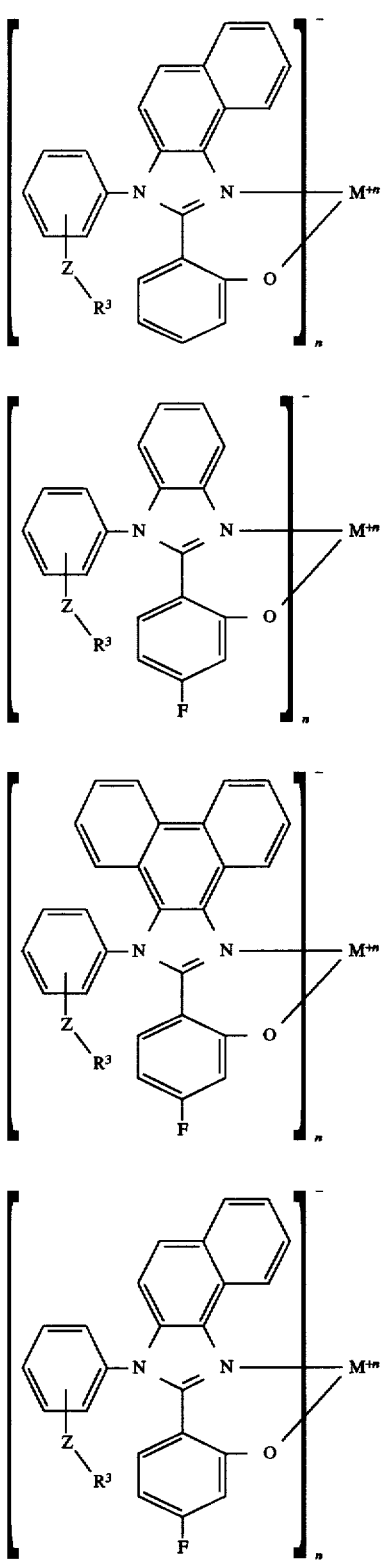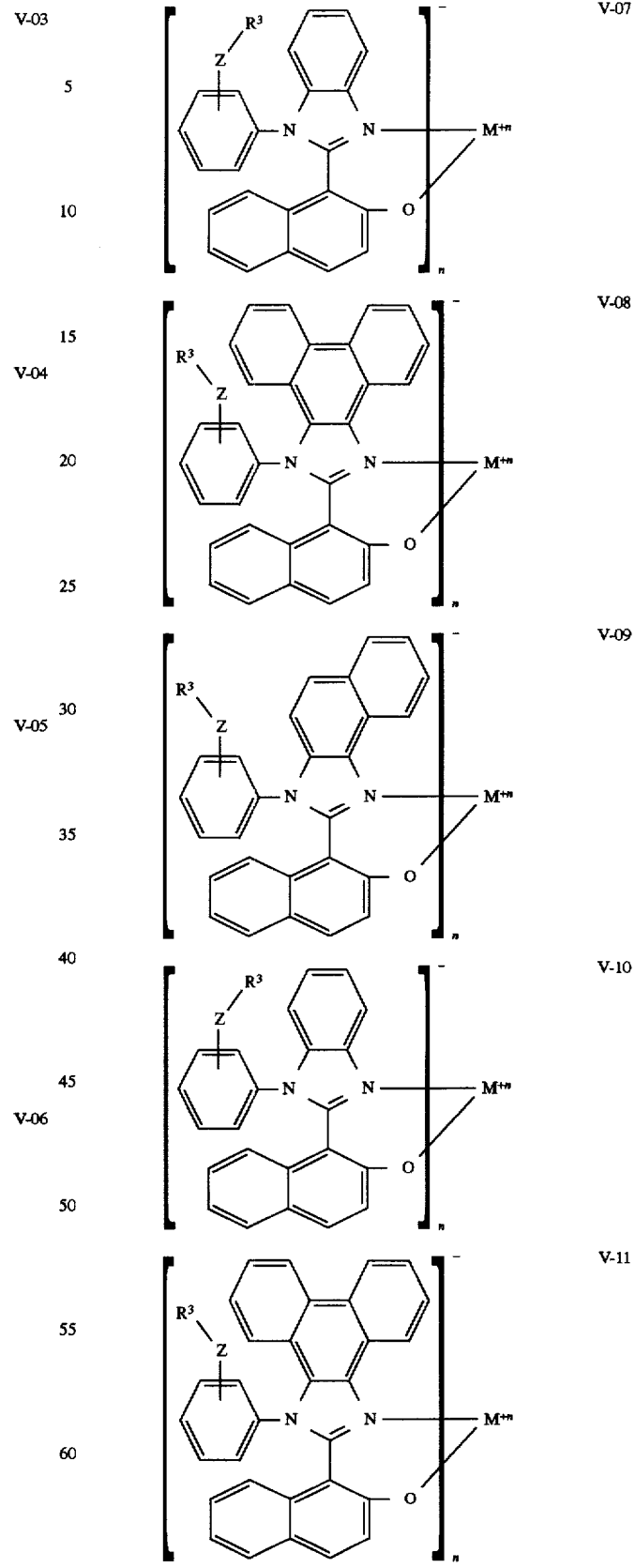

V-12
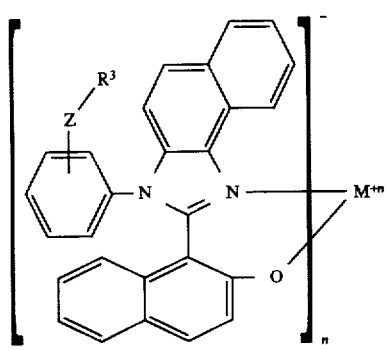

V-13
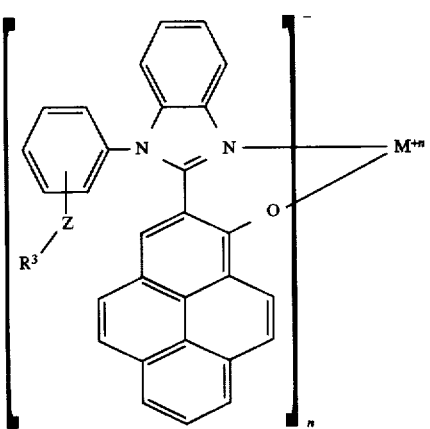

V-14
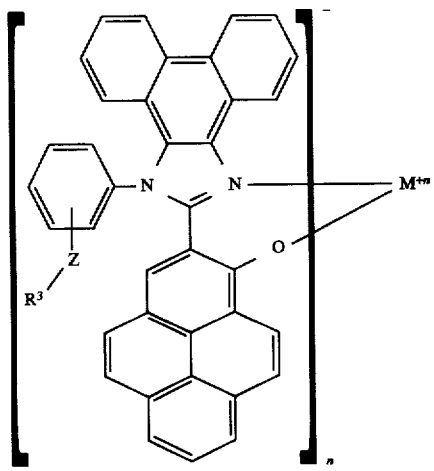

V-15
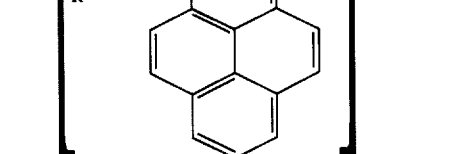

where:
n is an integer of 2 or 3;
M is a divalent metal or a trivalent metal;
When n=2, M is a divalent metal selected from the group consisting of Be, Mg, Sr, Ba, Ca, Zn, Cd, Hg, Pd, and Cu;
When n=3, M is a trivalent metal selected from the group consisting of Al, Ga, In, and Tl;
Z is O or S;
$R^4$ is individually an alkyl having 1–18 carbon atoms, aryl group, and 5–24 atoms necessary to complete a fused aromatic ring.

Group VI:

VI-01
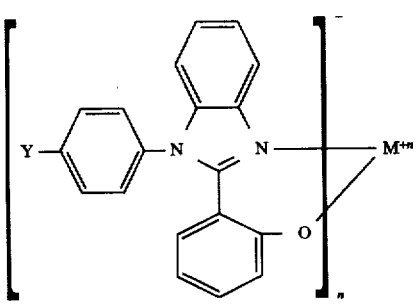

VI-02
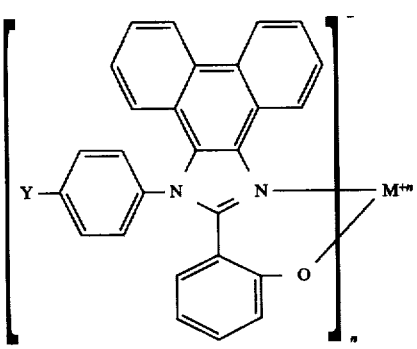

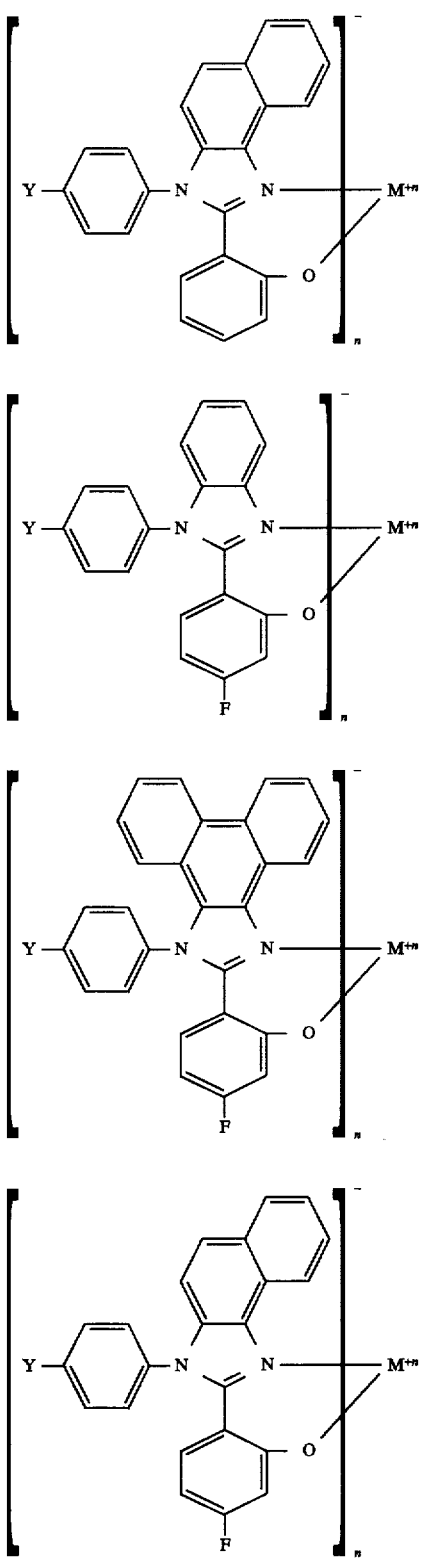
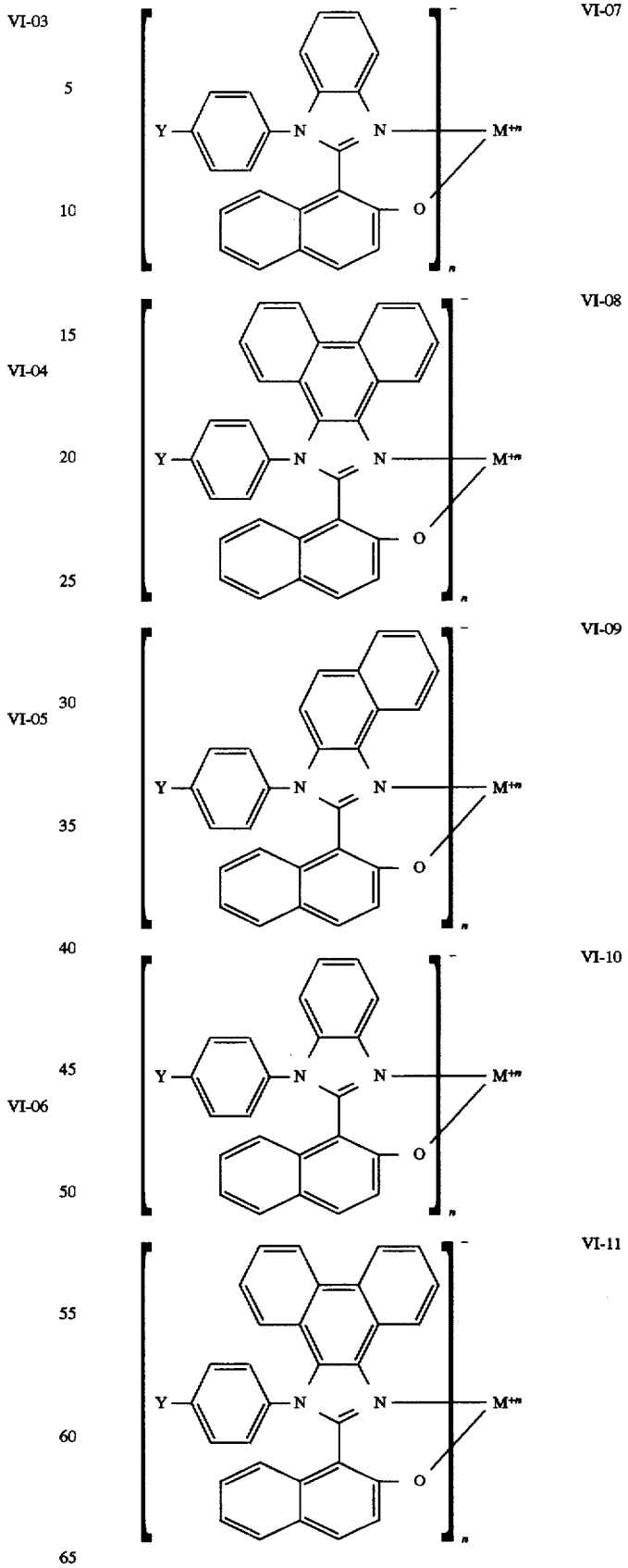

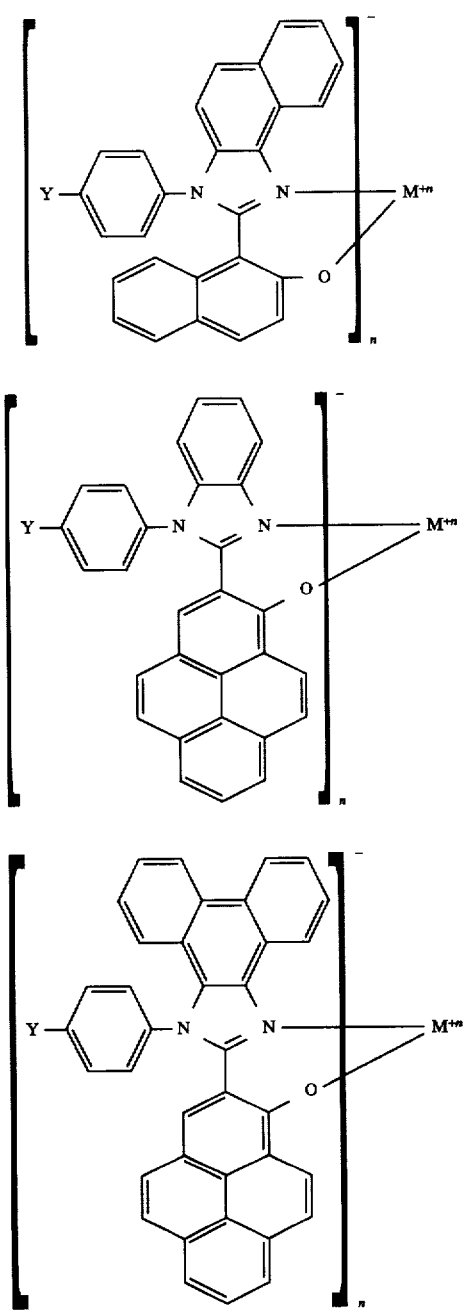

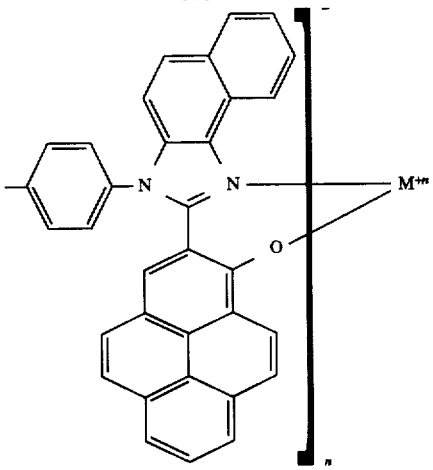

where:

n is an integer of 2 or 3;

M is a divalent metal or a trivalent metal;

When n=2, M is a divalent metal selected from the group consisting of Be, Mg, Sr, Ba, Ca, Zn, Cd, Hg, Pd, and Cu;

When n=3, M is a trivalent metal selected from the group consisting of Al, Ga, In, and Tl;

Y is $NR^5R^6$;

$R^5$ and $R^6$ is individually a hydrogen, an alkyl group having 1–18 carbon atoms, aryl group, and 5–24 atoms necessary to complete a fused aromatic ring.

The luminescent materials of the present invention can be prepared by following sequence.

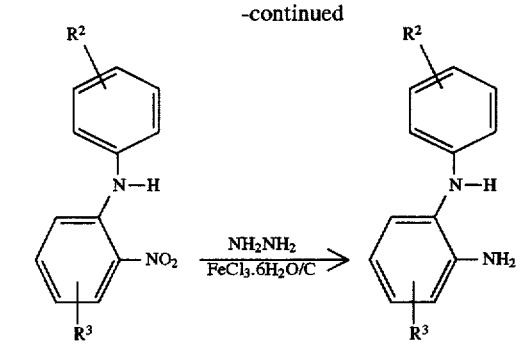
(2)

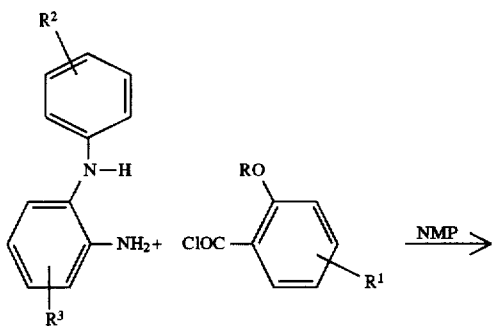
(3)

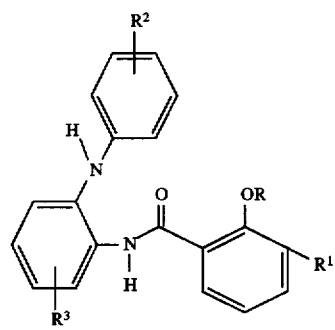
(4)

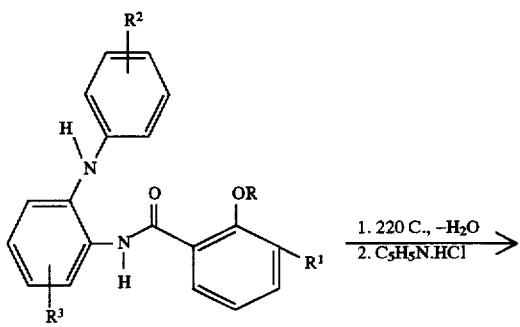

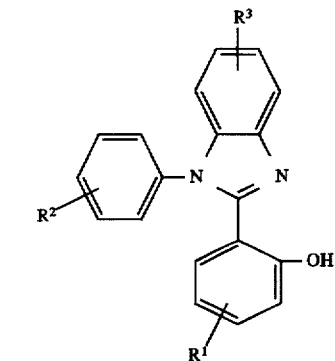

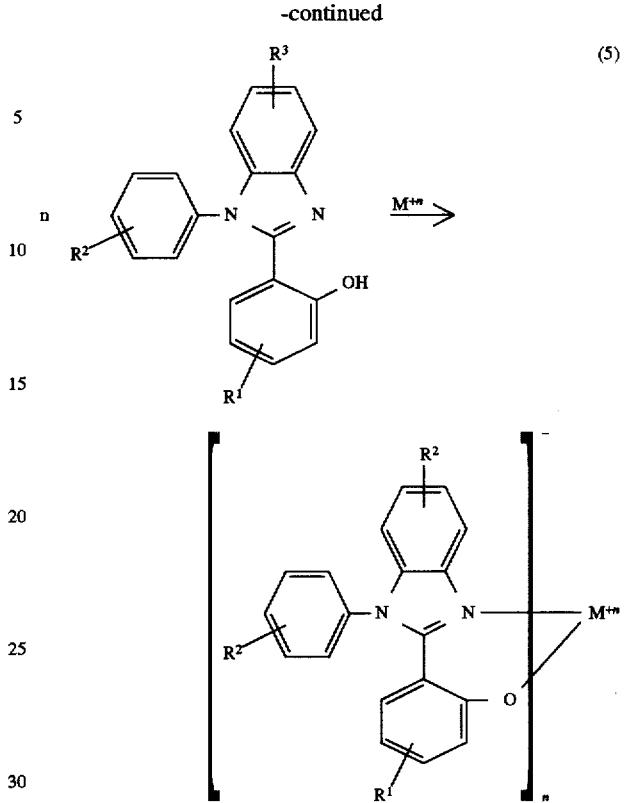
(5)

where:

n is an integer of 2 or 3;

M is a divalent metal or a trivalent metal;

When n=2, M is a divalent metal selected from the group consisting of Be, Mg, Sr, Ba, Ca, Zn, Cd, Hg, Pd, and Cu;

When n=3, M is a trivalent metal selected from the group consisting of Al, Ga, In, and Tl;

R, $R^1$, $R^2$ and $R^3$ is individually a hydrogen, an alkyl group having 1–18 carbon atoms, aryl group, and 5–24 atoms necessary to complete a fused aromatic ring.

Preferred materials for use in forming the electron transporting layer of the organic EL devices of this invention are metal chelated oxinoid compounds, including chelates of oxine itself (also commonly referred to as 8-quinolinol or 8-hydroxyquinoline). Such compounds exhibit both high levels of performance and are readily fabricated in the form of thin films. Exemplary of contemplated oxinoid compounds are those satisfying the following structural formula:

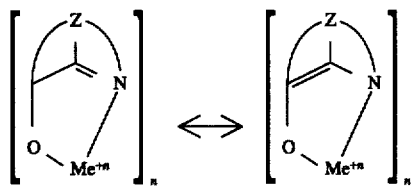

wherein

Me represents a metal;

n is an integer of from 1 to 3; and

Z independently in each occurrence represents the atoms completing a nucleus having at least two fused aromatic rings.

From the foregoing it is apparent that the metal can be monovalent, divalent, or trivalent metal. The metal can, for example, be an alkali metal, such as lithium, sodium, or potassium; an alkaline earth metal, such as magnesium or calcium; or an earth metal, such as boron or aluminum. Generally any monovalent, divalent, or trivalent metal known to be a useful chelating metal can be employed.

Z completes a heterocyclic nucleus containing at least two fused aromatic rings, at least one of which is an azole or azine ring. Additional rings, including both aliphatic and aromatic rings, can be fused with the two required rings, if required. To avoid adding molecular bulk without improving on function the number of ring atoms is preferably maintained at 18 or less.

Illustrative of useful chelated oxinoid compounds are the following:
Aluminum trisoxine [a.k.a. tris(8-quinolinol)aluminum]
Magnesium bisoxine [a.k.a. bis(8-quinolinol)-magnesium]
Indium trisoxine [a.k.a. tris(8-quinolinol)indium]
Lithium oxine (a.k.a. 8-quinolinol lithium)

The preferred materials for the multi-layers of the organic EL medium are each capable of film-forming—that is, capable of being fabricated as a continuous layer having a thickness of less than 5000 Å. A preferred method for forming the organic EL medium is by vacuum vapor deposition. Extremely thin defect-free continuous layers can be formed by this method. Specifically, the individual layer thickness as low as about 50 Å can be constructed while still realizing satisfactory EL device performance. It is generally preferred that the overall thickness of the organic EL medium be at least about 1000 Å.

Other methods for forming thin films in EL devices of this invention include spin-coating from a solution containing the EL material. A combination of spin-coating method and vacuum vapor deposition method is also useful for the fabrication of multi-layer EL devices.

The anode and cathode of the organic EL device can each take any convenient conventional form. Where it is intended to transmit light from the organic EL device through the anode, this can be conveniently achieved by coating a thin conductive layer onto a light transparent substrate—e.g., a transparent or substantially transparent glass plate or plastic film. In one form the organic EL devices of this invention can follow the historical practice of including a light transparent anode formed of tin oxide or indium tin oxide coated on a glass plate, as disclosed by Gurnee et al U.S. Pat. No. 3,172,862, Gurnee U.S. Pat. No. 3,173,050, Dresner "Double Injection Electroluminescence in Anthracene", *RCA Review*, Volume 30, pages 322–334, 1969; and Dresner U.S. Pat. No. 3,710,167 cited above.

The organic EL devices of this invention can employ a cathode constructed of any metal, including any high or low work function metal, heretofore taught to be useful for this purpose. Unexpected fabrication, performance, and stability advantages have been realized by forming the cathode of a combination of a low work function metal and at least one other metal. For further disclosure, see U.S. Pat. No. 4,885, 211 by Tang and Van Slyke, the disclosure of which is incorporated by reference herein.

EXAMPLES

The invention and its advantages are further illustrated by the examples as follows:

Material Preparation

Example 1

Synthesis of 2-(N-biphenyl)-nitrobenzene 4-aminobiphenyl (21.52 g, 0.1274 mol) and sodium bicarbonate (10.7 g, 0.1274 mol) were placed under a nitrogen atmosphere and heated at 130°–150° C. for 3 hours to remove water. Then, 1-chloro-2-nitrobenzene (20.1 g, 0.128 mol) was added and the mixture was heated at 185°–195° C. overnight. The mixture was cooled. Dichloromethane and acidic water were added and the layers were separated. The organic layer was washed with water, dried over sodium sulfate and concentrated to give a dark brown solid. The solid was dissolved in a minimal amount of dichloromethane:hexane (1:1) mixture and passed through a silica gel column using dichloromethane:hexane (1:1) as eluent. After removal of solvents, the crude red product was then recrystalized from acetonitrile to give 2-(N-biphenyl)-1-nitrobenzene as red needle crystals weighing 18.14 g in a yield of 49%.

Example 2

Synthesis of N-biphenyl-1,2-phenylenediamine

The material of Example 1, 2-(N-biphenyl)-nitrobenzene (10.22 g, 0.0352 mol) was dissolved in 135 ml of methanol. To this solution was added 1.39 g Norit and 0.58 g ferric chloride hexahydrate. This mixture was placed under nitrogen and heated to reflux. After 20 min, hydrazine (19.1 ml, 0.5969 mol) was added slowly over 45 minutes and the mixture continued to heat at reflux for 12 hrs. The solution was cooled to room temperature and then filtered. The norit was washed with dichloromethane. The filtrate was evaporated and the crude product was dissolved in dichloromethane. After washing with water, the organic layer was dried over sodium sulfate and concentrated to give 9.0 g of N-biphenyl-1,2-phenylenediamine as a white solid in a yield of 98.3%.

Example 3

Synthesis of 1-(N-biphenyl)-2-[N'-(2'-methoxyphenylamino)] benzamide

The material of Example 2, N-biphenyl-1,2-phenylenediamine (7.0 g, 0.0269 mol) was dissolved in 27 ml N-methyl-2-pyrrolidinone (NMP) and o-anisoyl chloride (4.6 g, 0.0269 mol) was then added to the solution at room temperature under nitrogen. The reaction mixture was stirred for 3 hours at room temperature and then the reaction temperature was increased to 50° C. for 30 min. After cooling the solution was poured to 100 ml of cool water with stirring. The resulting precipitates were filtered and washed with water to give 10.4 g of product in a yield of 98%.

Example 4

Synthesis of o-(1-biphenyl-2-benzimidazolyl) phenol

The material of Example 3, 1-(N-biphenyl)-2-[N'-(2'-methoxyphenylamino) benzamide (9.8 g, 0.0249 mol) was heated in a 100 ml round bottom flask at 220° C. under 0.3 atm. nitrogen pressure for about 5 hours. After starting material was completely converted to product (checked by TLC), the reaction was cooled to 100° C. and 15.86 g of pyridine hydrochloride was added and the solution was then heated to reflux (around 200°–210° C.) for 4 hours. The reaction was cooled to room temperature and then dissolved in dichlorometane. Pyridine chloride was removed by washing with water. The methylene chloride solution was passed through a silica gel column using methylene chloride as eluent to remove the dark-brown colorants. After removal of solvents the product was heated in ethanol. After cooling to room temperature, the mixture was filtered to give 7.06 g of product as a brown solid for a yield of 78.4%.

Example 5

Synthesis of tris-[2-(2'-hydroxyphenyl)-1-biphenyl-1Hbenzimidazolate] aluminum [Al(BPBI)$_3$] Compound II-01 where n=3, M=Al)

The material of Example 4 o-(1-biphenyl-2-benzimidazolyl) phenol (2.0 g, 5.525 mmol) was prepared and dissolved in 70 ml toluene. Then, triisobutyl aluminum (1.75 ml, 1.84 mmol, d=0.848, 25 wt. % (1.0M) soln.) was added and the mixture was heated to reflux. After 20 minutes, a white solid precipitated out of solution and the mixture was allowed to reflux for an additional 3 hours. After cooling to room temperature the mixture was filtered and washed with cold toluene to give 1.99 g of white solid product in a yield of 97.6%.

Example 6

Synthesis of 1-(N-phenyl)-2-[N'-(2'-methoxyphenylamino)] benzamide

To a solution of N-phenyl-1,2-phenylenediamine (9.2 g, 0.05 mol) in 50 mL of N-methyl pyrrolidinone was gradually added o-anisonyl chloride (8.5 g, 0.05 mol) by syringe at room temperature under nitrogen. The reaction mixture was stirred at room temperature for two hours and then the reaction temperature was raised to 50° C. for another half hour. After cooling to room temperature the reaction mixture was poured into 200 ml of cool water with stirring. The resulting precipitates were filtered and washed with water. After drying, the 1-(N-phenyl)-2-[N-(2'-methoxyphenylamino)]benzamide was collected and weighed 15.2 g in a yield of 96%.

Example 7

Synthesis of o-(N-phenyl-2-benzimidazolyl) phenol Method A

The material of Example 6, 1-(N-phenyl)-2-[N'-(2'-methoxyphenylamino)]benzamide (10.2 g, 0.032 mol) was heated in a 100 mL three neck flask at 220° C. under 0.3 atm. nitrogen pressure for about three hours. After the starting material was completely converted to benzimidazole (checked by TLC) the reaction was cooled to 100° C., and then 20 g of pyridine hydrochloride was added. The reaction mixture was heated to reflux (around 200° C.) for three hours. After cooling to room temperature it was dissolved in 100 mL of methylene chloride. Pyridine chloride was removed by washing out with water. The methylene chloride solution was passed through silican gel column with methylene chloride as eluant to remove dark-brown colorants. After removal of solvents the crude product was crystalized from ethanol to give o-(N-phenyl-2-benzimidazolyl) phenol in the form of needle crystals and weighed 7.4 g in a yield of 80.4%.

Example 8

Synthesis of o-(N-phenyl-2-benzimidazolyl) phenol Method B

N-phenyl-1,2-phenylenediamine (25 g, 0.136 mol) was dissolved in 100 ml N-methyl-2-pyrrolidinone (NMP) and o-anisoyl chloride (23.2 g, 0.136 mol) was then added to the solution at room temperature under nitrogen. The reaction mixture was stirred for 30 minutes at room temperature and then the temperature was increased to 220° C. for three hours during which time a white solid precipitated out of solution. After cooling, 150 ml of water was added to the reaction mixture and product was extracted with 300 ml of dichloromethane. The organic layer was washed with water and then dried with sodium sulfate. After removal of the solvents, the desired product o-(N-phenyl-2-benzimidazolyl) anisole was obtained.

As prepared above, o-(N-phenyl-2-benzimidazolyl) anisole was placed into a round bottom flask. 50 g of pyridine hydrochloride was added and the flask was heated to reflux (around 200°–210° C.) for 4 hours. The reaction was cooled to room temperature and then dissolved in methylene chloride. This solution was washed with water to remove the pyridine chloride. The organic layer was passed through a silica gel column using methylene chloride as eluent to remove the dark-brown colorants. After removal of solvents the crude product was recrystalized from ethanol to give 25.76 g of pure product o-(1-phenyl-2-benzimidazolyl) phenol in a yield of 66%.

Example 9

Synthesis of tris-[2-(2'-hydroxyphenyl)-1-phenyl-1H-benzimidazolate]aluminum [Al(PBI)$_3$] (compound I-01, where n=3, M=Al)

The material of Example 7, o-(N-phenyl-2-benzimidazolyl) phenol (5.73 g, 0.02 mol) was dissolved in 75 mL of dry ethanol at refluxing. To this above solution was added aluminum isopropoxide (1.36 g, 0.67 mol) under nitrogen. The reaction mixture was refluxed for two and half hours. The precipitates were filtered and washed with ethanol. After drying tris-[2-(2'-hydroxyphenyl)-1-phenyl-1H-benzimidazolate] aluminum weighed 5.4 g in a yield of 91.5%.

The tis-[2-(2'-hydroxyphenyl)-1-phenyl-1H-benzimidazolate] aluminum (3.0 g) obtained from above was placed into a pyrex glass boat and was sublimated using a minioven at 345° C. under constant 2 torr argon pressure. The sublimed material was collected and weighed 2.3 g in a yield of 76.7%.

Example 10

Synthesis of bis-[2-(2-hydroxyphenyl)-1-phenyl-1H-benzimiidazolate] beryllium [Be(PBI)$_2$]] (compound I-01, where n=2, M=Be)

The material of Example 7, o-(N-phenyl-2-benzimidazolyl) phenol (2.86 g, 0.01 mol) was dissolved in 60 mL of dry ethanol at refluxing. To this above solution was added beryllium sulfate tetrahydrate (0.9 g, 0.005 mol in 2 ml of water) with stirring. The reaction mixture was adjusted to a pH value of about 12 by adding 2.0N solution of sodium hydroxide. The reaction was heated under refluxing for a half hour and the precipitates were filtered while hot. The precipitates were washed with ethanol and dried in an oven. Bis-[2-(2'-hydroxyphenyl)-1-phenyl-1H-benzimidazolate] beryllium was obtained and weighed 2.8 g in a yield of 96.5%.

The bis-[2-(2'-hydroxyphenyl)-1-phenyl-1H-benzimidazolate] beryllium (2.8 g) obtained from example 6 was placed into pyrex glass boat and was sublimated using a minioven at 345° C. under constant 2 torr argon pressure. The sublimed material was collected and weighed 2.0 g in a yield of 71.4%.

Example 11

Synthesis of tris-[2-(2'-hydroxyphenyl)-1-phenyl-1H-benzimidazolate]zinc [Zn(PBI)$_2$] (compound I-01, where n=2, M=Zn)

The material of Example 7, o-(N-phenyl-2-benzimidazolyl) phenol (2.87 g, 0.01 mol) was dissolved in 50 mL of dry ethanol at refluxing. To this above solution was added zinc acetate dihydrate (1.10 g, 0.005 mol) under nitrogen. The reaction mixture was refluxed for two and half hours. The precipitates were filtered and washed with ethanol. After drying tris-[2-(2'-hydroxyphenyl)-1-phenyl-1H-benzimidazolate]zinc weighed 2.80 g in a yield of 88.0%.

Example 12

Synthesis of tris-[2-(2'-hydroxyphenyl)-1-phenyl-1H-benzimidazolate] Copper(II) [Cu(PBI)$_2$] (compound I-01, where n=2, M=Cu)

The material of Example 7, o-(N-phenyl-2-benzimidazolyl) phenol (2.87 g, 0.01 mol) was prepared and dissolved in 50 mL of dry ethanol at refluxing. To this above solution was added copper acetate dihydrate (1.0 g, 0.005 mol) under nitrogen. The reaction mixture was refluxed for two and half hours. The precipitates were filtered and washed with ethanol. After drying, tris-[2-(2'-hydroxyphenyl)-1-phenyl-'H-benzimidazolate] copper(II) weighed 2.82 g in a yield of 89.0%.

Example 13

Synthesis of tris-[2-(2'-hydroxyphenyl)-1-phenyl-1H-benzimidazolate] magnesium [Mg(PBI)$_2$] (compound I-01, where n=2, M=Mg)

The material of Example 7, o-(N-phenyl-2-benzimidazolyl) phenol (2.87 g, 0.01 mol) was prepared and dissolved in 50 mL of dry ethanol at refluxing. To this above solution was added magnesium acetate tetrahydrate (1.07 g, 0.005 mol) under nitrogen. The reaction mixture was refluxed for two and half hours. The precipitates were filtered and washed with ethanol. After drying tris-[2-(2-hydroxyphenyl)-1-phenyl-1Hbenzimidazolate] magnesium weighed 2.80 g in a yield of 87.0%.

EL Device Fabrication and Performance

Example 14

An EL device satisfying the requirements of the invention was constructed in the following manner. The organic EL medium has four organic layers, namely, a hole-injection layer, a hole transport layer, a luminescent layer, and an electron-transport layer a) An indium-tin-oxide (ITO) coated glass substrate was sequentially ultrasonicated in a commercial detergent, rinsed in deionized water, degreased in toluene vapor and exposed to ultraviolet light and ozone for a few minutes.

b) A hole injection layer of copper phthalocyanine (150 Angstroms) was then deposited on top of the ITO coated substrate by evaporation from a tantalum boat.

c) Onto the copper phthalocyanine layer was deposited a hole transport layer of N,N'-bis-(1-naphthyl)-N,N'-diphenylbenzidine (600 Angstroms), also by evaporation from a tantalum boat.

d) A luminescent layer of bis-[2-(2'-hydroxyphenyl)-1-phenyl-1H-benzimidazolate] beryllium [Be(PBI)$_3$] from example 6 (300 Angstroms) was then deposited onto the hole-transport layer by evaporation from a tantalum boat.

e) A electron-transport layer of Alq (375 Angstroms) was then deposited onto the luminescent layer by evaporation from a tantalum boat.

f) On top of the Alq layer was deposited by evaporation a cathode layer (2000 Angstroms) formed of a 10:1 atomic ratio of Mg and Ag.

The above sequence completed the deposition of the EL device. The device was then hermetically packaged in a dry glove box for protection against ambient environment.

The light output from this EL device was 337 cd/m$^2$ when it was driven by a current source at 20 mA/cm$^2$ and at a bias voltage of 11.5 volts. The EL color is blue with 1931 CIE color coordinates of X=0.158 and Y=0.168.

Example 15

An EL device satisfying the requirements of the invention was constructed in the following manner. The organic EL medium has three organic layers, namely, a hole-injection layer, a hole transport layer, and an electron-transport luminescent layer.

a) An indium-tin-oxide (ITO) coated glass substrate was sequentially ultrasonicated in a commercial detergent, rinsed in deionized water, degreased in toluene vapor and exposed to ultraviolet light and ozone for a few minutes.

b) A hole injection layer of copper phthalocyanine (150 Angstroms) was then deposited on top of the ITO coated substrate by evaporation from a tantalum boat.

c) Onto the copper phthalocyanine layer was deposited a hole transport layer of N,N'-bis-(1-naphthyl)-N,N'-diphenylbenzidine (600 Angstroms), also by evaporation from a tantalum boat.

d) A electron-transport luminescent layer of tris-[2-(2'-hydroxyphenyl)-1-phenyl-1H-benzimidazolate] aluminum [Al(PBI)$_3$] from example 4 (400 Angstroms) was then deposited onto the hole-transport layer by evaporation from a tantalum boat.

e) On top of the electron-transport luminescent layer was deposited by evaporation a cathode layer (2000 Angstroms) formed of a 10:1 atomic ratio of Mg and Ag.

The above sequence completed the deposition of the EL device. The device was then hermetically packaged in a dry glove box for protection against ambient environment.

The light output from this EL device was 216 cd/m$^2$ when it was driven by a current source at 20 mA/cm$^2$ and at a bias voltage of 11.0 volts. The EL color is blue with 1931 CIE color coordinates of X=0.153 and Y=0.125.

Example 16

An EL device satisfying the requirements of the invention was constructed in the following manner. The organic EL medium has three organic layers, namely, a hole-injection layer, a hole transport layer, and an electron-transport luminescent layer.

a) An indium-tin-oxide (ITO) coated glass substrate was sequentially ultrasonicated in a commercial detergent, rinsed in deionized water, degreased in toluene vapor and exposed to ultraviolet light and ozone for a few minutes.

b) A hole injection layer of copper phthalocyanine (150 Angstroms) was then deposited on top of the ITO coated substrate by evaporation from a tantalum boat.

c) Onto the copper phthalocyanine layer was deposited a hole transport layer of N,N'-bis-(1-naphthyl)-N,N'-diphenylbenzidine (600 Angstroms), also by evaporation from a tantalum boat.

d) A electron-transport luminescent layer of tris-[2-(2'-hydroxyphenyl)-1-phenyl-1H-benzimidazolate] beryllium [Be(PBI)$_2$] from example 6 (400 Angstroms) was then deposited onto the hole-transport layer by evaporation from a tantalum boat.

e) On top of the electron-transport luminescent layer was deposited by evaporation a cathode layer (2000 Angstroms) formed of a 10:1 atomic ratio of Mg and Ag.

The above sequence completed the deposition of the EL device. The device was then hermetically packaged in a dry glove box for protection against ambient environment.

The light output from this EL device was 504 cd/m$^2$ when it was driven by a current source at 20 mA/cm$^2$ and at a bias voltage of 8.7 volts. The EL color is blue with 1931 CIE color coordinates of X=0.154 and Y=0.151.

The invention has been described in detail with particular reference to certain preferred embodiments thereof, but it will be understood that variations and modifications can be effected within the spirit and scope of the invention.

PARTS LIST

100 EL Device
102 Substrate
104 Anode
106 Cathode
108 Organic EL medium
110 Hole-transport layer
112 Electron-transport layer
114 External power source
116 Conductor
118 Conductor
120 Holes
122 Electrons
200 EL device
202 Substrate
204 Anode
206 Cathode
208 Organic EL medium
210 Hole-transport layer
212 Luminescent layer
214 Electron-transport layer
300 EL device
302 Substrate
304 Anode
306 Cathode
308 Organic EL medium
310 Hole-injection layer
312 Hole-transport layer
314 Luminescent layer
316 Electron-transport layer
318 Electron-injection layer

What is claimed is:

1. A luminescent material including a compound of the formula:

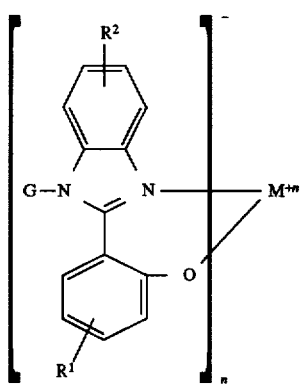

where:
n is an integer of 2 or 3;
M is a divalent metal or a trivalent metal;
G is a substituted or unsubstituted aryl group or a substituted or unsubstituted heteroaryl group, both the aryl and the heteroaryl groups having 6 to 24 carbon atoms, wherein the substituted aryl or heteroaryl group is an alkyl, haloalkyl group having 1–8 carbon atoms, an alkoxy or haloalkoxy group having 1–18 carbon atoms, halogen, cyano, amino, amido, sulfonyl, carbonyl, aryl, or heteroaryl; and $R^1$ and $R^2$ are individually hydrogen, an alkyl or haloalkyl group having 1–18 carbon atoms, halogen, cyano, amono, amido, sulfonyl, carbonyl, and 5–24 atoms necessary to complete a fused aromatic ring.

2. The luminescent compound according to claim 1, wherein the metal M is a divalent metal selected from the group consisting of Be, Mg, Sr, Ba, Ca, Zn, Cd, Hg, Pd, and Cu and when n equals 2, and when n equals 3 the metal M is a trivalent metal selected from the group consisting of Al, Ga, In, and Tl.

3. The luminescent compounds according to claim 1, when G is a substituted or unsubstituted aryl group, it includes a substituted or unsubstituted heteroaryl group including naphthyl, anthracenyl pyrenyl, perylenyl, pyridinyl, thiophenyl, quinolinyl, or acridinyl.

4. The luminescent compound according to claim 1, wherein the fused aromatic ring formed by $R^1$ and $R^2$ includes naphthyl, anthracenyl pyrenyl, or perylenyl.

5. A luminescent compound comprising an anode, cathode, and at least one organic luminescent layer including a compound of the formula:

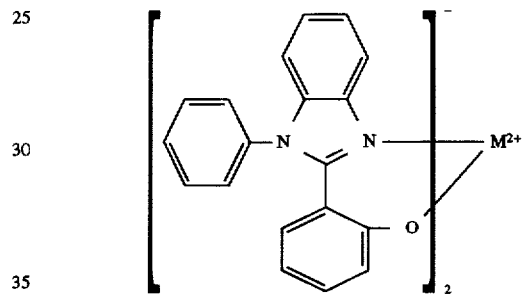

wherein M is a divalent metal selected from the group consisting Be, Mg, Ca, Zn, and Cu.

6. A luminescent compound, comprising an anode, cathode, and at least one organic luminescent layer including a compound of the formula:

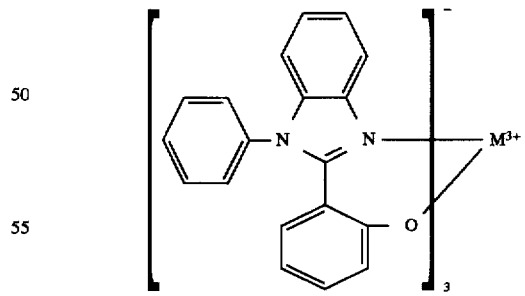

wherein M is a trivalent metal selected from the group Al, Ga, In, and Tl.

7. A luminescent compound, comprising an anode, cathode, and at least one organic luminescent layer including a compound of the formula:

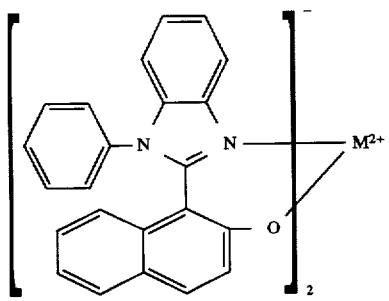
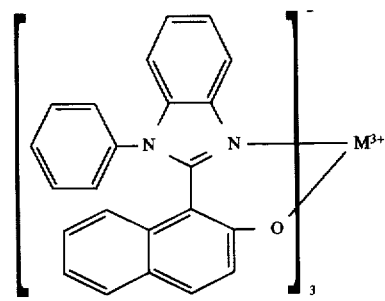
wherein M is a divalent metal selected from the group consisting Be, Mg, Ca, Zn, and Cu.
8. A luminescent compound, comprising an anode, cathode, and at least one organic luminescent layer including a compound of the formula:
wherein M is a trivalent metal selected from the group Al, Ga, In, and Tl.
* * * * *